United States Patent [19]
Keller et al.

[11] Patent Number: 5,893,974
[45] Date of Patent: Apr. 13, 1999

[54] MICROFABRICATED CAPSULES FOR IMMUNOLOGICAL ISOLATION OF CELL TRANSPLANTS

[75] Inventors: Christopher G. Keller, Albany; Mauro Ferrari, Walnut Creek, both of Calif.

[73] Assignee: Regents of University of California, Oakland, Calif.

[21] Appl. No.: 08/254,330

[22] Filed: Jun. 6, 1994

Related U.S. Application Data

[63] Continuation-in-part of application No. 08/207,459, Mar. 7, 1994, Pat. No. 5,660,680, which is a continuation-in-part of application No. 08/207,457, Mar. 7, 1994, Pat. No. 5,651,900.

[51] Int. Cl.$^6$ .......................... B01D 69/10; A61K 9/52
[52] U.S. Cl. .......................... 210/483; 210/500.26; 216/56; 264/4; 424/424; 427/245; 428/312.6; 604/891.1
[58] Field of Search ................ 210/321.87, 321.88, 210/500.22, 500.26, 500.27, 650, 651; 264/4, 42, 43, 45.1, 45.2, 45.5; 424/424, 451, DIG. 7; 435/176, 240.22; 604/890.1, 891.1, 892.1; 428/312.6, 402; 423/338, 339, 348, 349, 350; 156/145

[56] References Cited

U.S. PATENT DOCUMENTS

| | | |
|---|---|---|
| 3,556,945 | 1/1971 | Messing . |
| 3,791,987 | 2/1974 | Fanger .................. 264/4 |
| 3,841,971 | 10/1974 | Messing . |
| 3,962,052 | 6/1976 | Abbas et al. ............ 204/129.2 |
| 4,078,971 | 3/1978 | Arkles et al. . |
| 4,409,331 | 10/1983 | Lim ...................... 435/178 |
| 4,455,143 | 6/1984 | Theeuwes et al. ........ 604/890.1 |
| 4,673,566 | 6/1987 | Goosen et al. ............ 424/19 |
| 4,743,545 | 5/1988 | Torobin ................. 435/41 |
| 4,793,825 | 12/1988 | Benjamin et al. ........ 604/891.1 |
| 4,797,211 | 1/1989 | Ehrfeld et al. .......... 210/321.84 |
| 4,841,228 | 6/1989 | Zentner et al. .......... 424/456 |
| 4,937,209 | 6/1990 | Jones et al. ............ 501/80 |
| 5,156,623 | 10/1992 | Hakamatsuka et al. .... 604/891.1 |
| 5,200,334 | 4/1993 | Dunn et al. ............ 501/12 |
| 5,225,123 | 7/1993 | Torobin ................. 264/43 |
| 5,230,693 | 7/1993 | Williams et al. ........ 600/36 |
| 5,238,613 | 8/1993 | Anderson ............... 264/22 |
| 5,314,471 | 5/1994 | Brauker et al. ......... 604/891.1 |
| 5,376,347 | 12/1994 | Ipponmatsu et al. ..... 423/338 |
| 5,431,921 | 7/1995 | Thombre ............... 424/424 |
| 5,453,278 | 9/1995 | Chan et al. ............ 424/424 |
| 5,585,011 | 12/1996 | Saaski et al. .......... 216/56 |
| 5,603,953 | 2/1997 | Herbig et al. .......... 424/451 |
| 5,629,008 | 5/1997 | Lee .................... 604/392.1 |
| 5,660,680 | 8/1997 | Keller ................. 438/50 |

FOREIGN PATENT DOCUMENTS

WO 93/23154  11/1993  WIPO .

OTHER PUBLICATIONS

G. Kittilsland et al., "A Sub-micron Particle Filter in Silicon," *Sensors and Actuators*, A21-A23, (1990), pp. 904-907.

W. Lang et al., "Application of Porous Silicon as a Sacrificial Layer," *7th International Conference on Solid-State Sensors and Actuators—Digest of Technical Papers*, Jun. 7-10, 1993, pp. 202-205.

Websters Miro New International Dictionary, Copyright©1986 by Merriam-Webster Inc., p. 811.

*Primary Examiner*—Joseph W. Drodge
*Attorney, Agent, or Firm*—Fish & Richardson P.C.

[57] ABSTRACT

The present invention provides a capsule made of a biologically compatible material with sufficient mechanical strength to form a very thin membrane shell having at least a region with approximately uniformly sized and spaced holes or pores that are large enough to let a desired biologically active molecular product through, while blocking the passage of all larger immunological molecules. The present invention thus provides an immunological isolation of cell transplants contained therein. The present invention also provides a free standing thin film structure that may be used as a component of such a capsule and method for the fabrication of such component and capsules.

11 Claims, 20 Drawing Sheets

MICROFABRICATED CAPSULES FOR IMMUNOLOGICAL ISOLATION OF CELL TRANSPLANTS

CROSS-REFERENCE TO RELATED APPLICATIONS

This application is a continuation-in-part of U.S. application Ser. No. 08/207,459, filed Mar. 7, 1994, now U.S. Pat. No. 5,660,680, which is a continuation of application Ser. No. 08/207,457, filed Mar. 7, 1994, now U.S. Pat. No. 5,651,900.

BACKGROUND OF THE INVENTION

The present invention relates generally to microfabricated capsules, and more particularly to microfabricated porous capsules for immunological isolation of cell transplants.

Medical researchers have demonstrated that the concept of microencapsulation to provide immunological isolation is valid. The islets of Langerhans, which produce insulin in mammals, have been transplanted between different species. For example, pig islets have been transplanted into diabetic dogs to produce insulin. However, these unprotected islets function only for a short time before the immune system of the host kills the donor cells.

Encapsulation of islets in order to protect them from immune system macromolecules has been shown to prolong the survival of donor cells. By using various means of encapsulation, insulin production from pig islets has been maintained for over one hundred days in dogs. Encapsulation methods to date have used semipermeable amorphous organic polymeric membranes, sintered together particles, and intermeshed ceramic needles. Significant problems have been encountered, however, limiting the useful life of these capsules to not much more than one hundred days.

The two principal problems with existing capsules are inadequate mechanical strength and insufficient control of pore size and pore distribution. Specifically, if the thickness of an organic membrane capsule wall is increased to provide the required mechanical strength, molecules cannot diffuse through the capsule wall quickly enough to provide the appropriate physiological response when needed. Moreover, if the size and distribution of pores cannot be controlled, such as with sintered together particles or amorphous polymeric membranes, there is a high probability of oversized or overlapping pores which could provide an opening large enough for immunological macromolecules to enter the capsule.

An improved capsule should combine mechanical strength with the ability to allow the free diffusion of small molecules such as oxygen, water, carbon dioxide, and glucose, while preventing the passage of larger molecules such as the immunoglobins and major histocompatibility (MHC) antigens. Also, the intermediate sized molecular products, such as insulin, produced by the donor cells should be able to diffuse out to the host at a sufficient rate to provide the needed metabolic function. Such a device would provide a longer lasting alternative to presently available capsules, and eliminate the need for anti-rejection drugs by the simple strategy of physically isolating the transplanted cells so that no immunological reaction can take place. Cells from any source could then be implanted in any host. Tissue matching of donor to recipient would not be a concern.

The ideal structure would be a capsule made of a biologically compatible material with sufficient mechanical strength to form a very thin membrane having at least a region with uniformly sized and spaced holes that are just large enough to let the desired biologically active molecular product through, while totally blocking the passage of all larger immunological molecules. Such a structure cannot be made from a polymer with an amorphous molecular structure, by sintering together particles, or by intermeshed ceramic needles.

Accordingly, an object of the present invention is to provide a capsule made of a biologically compatible material with sufficient mechanical strength to form a very thin membrane shell having at least a region with approximately uniformly sized and spaced holes in it that are large enough to let the desired biologically active molecular product through, while blocking the passage of all larger immunological molecules, thus providing an immunological isolation of cell transplants contained therein.

It is a further object of the present invention to provide a free standing thin film structure that may be used as a component of such a capsule.

It is another object of the present invention to provide methods for the fabrication of such components and such capsules.

Another object of the invention is to provide a method of filling such capsules.

Yet another object of the invention is to provide an apparatus for filling such capsules.

Still another object of the invention is to provide a method of administering a biologically active molecule to a host organism deficient in endogenous production of said biologically active molecule using such capsules.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention provides a containment capsule. The capsule has a shell composed of an inorganic material and at least one porous area in the shell with pores of predetermined, approximately uniform size and distribution. The shell provides a selective molecular barrier between the interior and the exterior of the capsule.

The invention also provides a free standing thin film structure that may be used as a component of such a capsule.

Also provided are methods for the fabrication of such structures and capsules by forming a mold in a substrate for a structure or capsule shell having at least one opening, coating the mold with a sacrificial layer, and growing a thin film on the sacrificial layer until the mold is filled. A completed structure may then be removed from the mold by removing the sacrificial layer.

If the structure is to form part of a more complex structure, such as the shell of a containment capsule, additional components may be formed on the shell prior to removing the sacrificial layer to remove the shell from the mold. An item to be contained within a space defined by said shell may then be placed therein, and the opening in said shell may be covered with a microfabricated thin-film membrane filter.

The invention also provides a method of filling a containment capsule by generating a fluid stream containing an item to be placed within a capsule across an opening in the capsule larger than the size of the item, and generating a second fluid stream from the first fluid stream, through the opening in the capsule. In this way, an item in the first stream is directed into the capsule by the second stream.

An apparatus for filling a containment capsule is also provided by the invention. The apparatus may have a hollow housing with a plurality of fluid access ports and means for securing a transfer wafer having porous-bottomed cavities bearing partially complete porous containment capsules on a front face within the housing, thereby dividing the housing into a first zone and a second zone. The apparatus also has a first pump and a reservoir connected by a first fluid access port in the housing to the first zone of the housing and a second pump connected by a second fluid access port in the housing to the second zone of the housing. A solution containing an item to be placed in the capsules is placed in the reservoir and supplied to the first zone by the first pump. The second pump generates a fluid flow from the first zone to the second zone through the porous capsules and wafer, thereby filling the capsules with the items in the solution which are too large to pass through the capsule pores.

In addition, the present invention provides a method of providing a biologically active molecule in a host organism by providing an inorganic, biocompatible microcapsule having controlled, predetermined, uniform pore size such that the pores permit diffusion of a biologically active molecule produced inside the microcapsule at a physiologically desirable rate, but prevent passage of immunological molecules located outside the microcapsule. The microcapsule is then filled with a cell, tissue, or pharmaceutical composition capable of producing a desired biologically active molecule, and administered to a host organism.

BRIEF DESCRIPTION OF THE DRAWINGS

The accompanying drawings, which are incorporated in and constitute a part of the specification, schematically illustrate a preferred embodiment of the invention and, together with the general description given above and the detailed description of the preferred embodiment given below, serve to explain the principles of the invention.

FIGS. 2H–2J, 2L–2O and 2Q are schematic perspective views of early stages in the fabrication process of a capsule according to the present invention.

DESCRIPTION OF THE PREFERRED EMBODIMENTS

The present invention will be described in terms of preferred embodiments. The preferred embodiments are microfabricated containment capsules or microcapsules, and methods for their fabrication. Also described are free standing, that is, unattached to a substrate, high vertical aspect ratio thin film structures useful in the fabrication of such capsules, and methods for their fabrication. A method and apparatus for filling microfabricated containment capsules, as well as a method for the use of the capsules in biological treatments are also described.

Figure 1A:
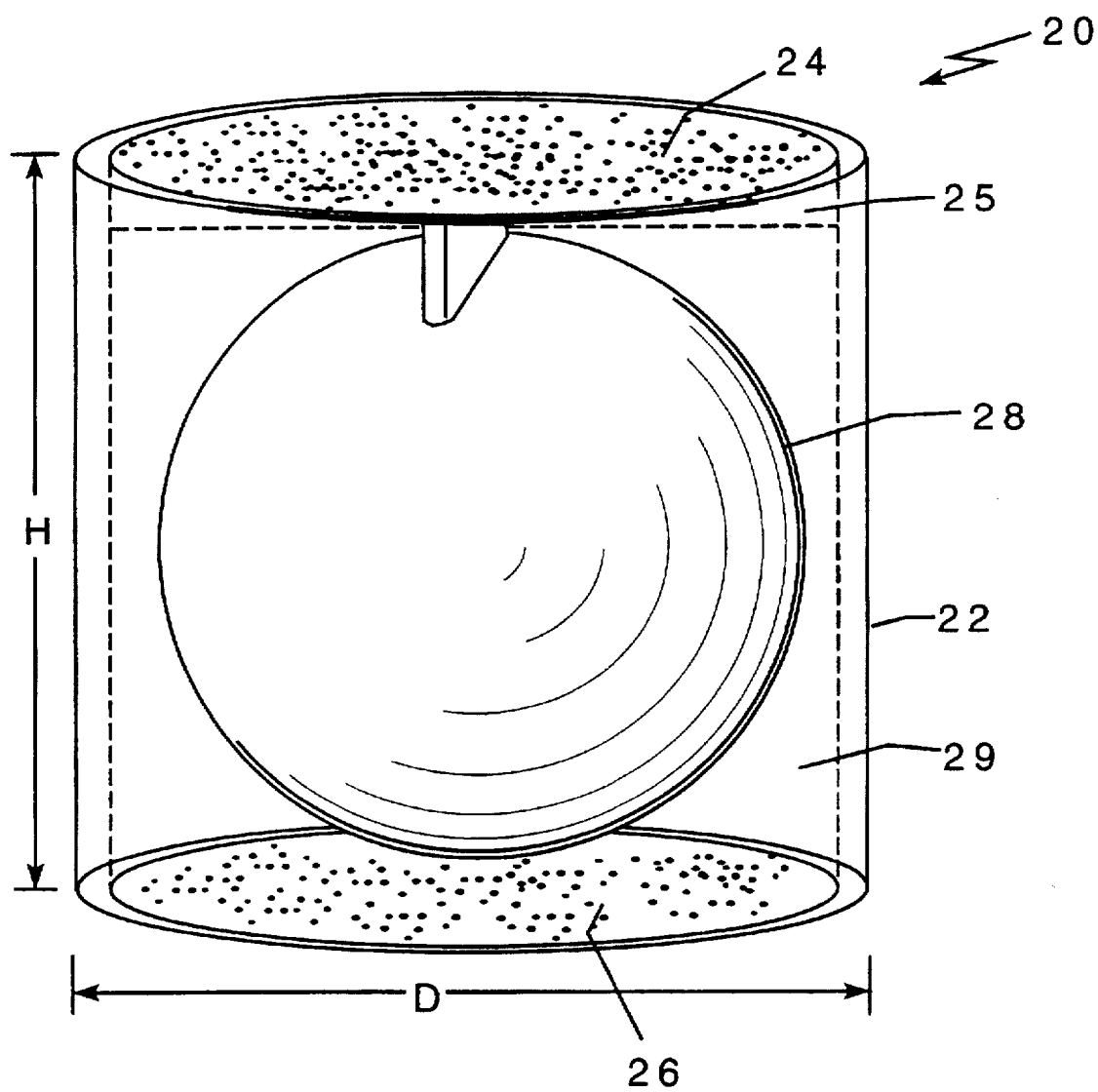
FIG. 1A is a schematic perspective view of a containment capsule in accordance with the present invention.

A containment capsule 20 according to the present invention is shown in FIG. 1A. The capsule 20 is a right cylinder with annular side walls 22, structural support members or ribs 25, and porous end faces 24 and 26. A cell, tissue, or pharmaceutical composition 28 may be contained in the lumen 29 of the capsule 20. The capsule 20 may be about 10 to about 2000 microns or more in diameter D and about 10 to about 1000 microns in height H.

The end faces 24 and 26 may be microfabricated particle filters, such as are described in applicants' commonly-assigned, patent application entitled MICROFABRICATED PARTICLE FILTER, Ser. No. 08/207,457, filed Mar. 7, 1994, now U.S. Pat. No. 5,657,900 which is hereby incorporated by reference in its entirety.

Figure 1B:
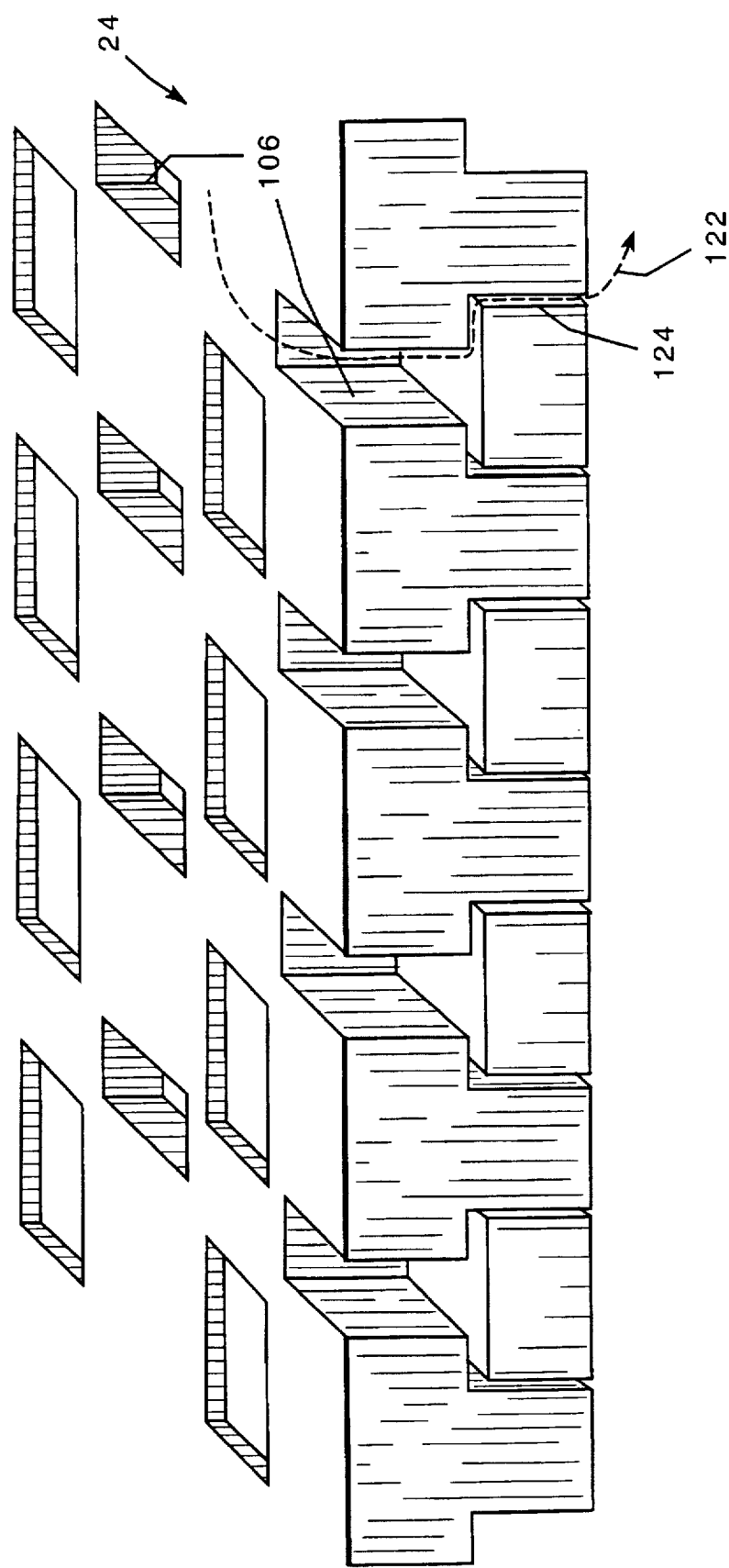
FIG. 1B is a schematic perspective sectional view of a microfabricated filter, which forms the end faces of the capsule of the present invention.

An example of such a filter is shown in FIG. 1B. Approximately uniformly distributed entrance passages 106 lead to very narrow, approximately uniformly sized pore channels 124 within the filter (capsule end face) 24. These pores 124 are selectively sized in the filter fabrication process such that they permit free diffusion of small molecules, such as water and glucose, across the capsule end faces 24 and 26, as shown by arrow 122, while blocking large macromolecules, such as immunoglobins. The pores may be from about 15 angstroms (Å) wide to about 1000 Å or more wide. The pores may be as small as 10 angstroms wide and as large as 3000 angstroms wide. The pores may be between about 20 and 50 angstroms wide.

Intermediate size molecules, such as insulin, are able to diffuse across the capsule end faces 24 and 26 at a physiologically desirable rate. Contained within the lumen 29 of the capsule 20, as noted, is a cell, tissue, or pharmaceutical composition 28, such as an islet of Langerhans, or a pharmaceutical composition, which produces a desired biologically active molecule, such as insulin.

Side walls 22 and ribs 25 having heights up to about 60 microns may be fabricated according to the methods herein described, or according to methods described in applicants' commonly-assigned patent application entitled, HIGH VER- TICAL ASPECT RATIO THIN FILM STRUCTURES, Ser. No. 08/207,459, now U.S. Pat. No. 5,660,680 filed Mar. 7, 1994, which is hereby incorporated by reference in its entirety.

The thin films forming side walls 22 and structural members 25 may be about 1 to about 6 microns thick, and, depending on structural requirements, may be formed into reinforced side walls 22 and support structures 25 from about 10 to about 50 microns or more thick. A schematic example of a side wall 22 with reinforcements 23 is shown in FIG. 2R.

Figure 2A:
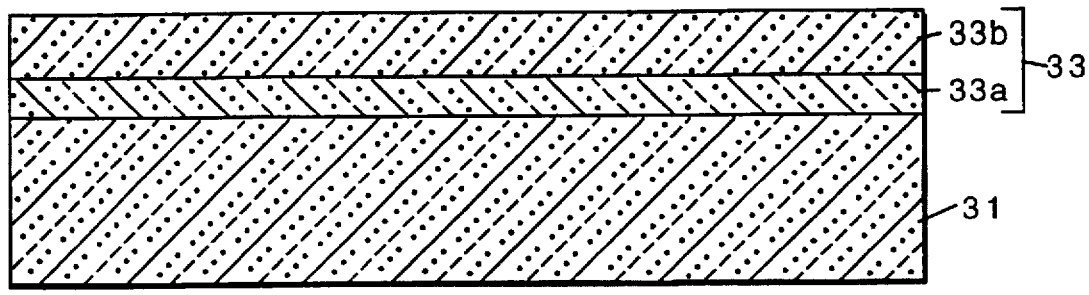
FIGS. 2A–2G are schematic sectional views of the first steps in the fabrication process according to the present invention.

The first steps in the fabrication of a mold for such a structure according to the present invention are shown in FIGS. 2A to 2G and FIG. 2H. As shown in FIG. 2A, a suitable substrate 31, such as an n-type (100) silicon wafer, is coated with a masking layer 33 of 0.2 to 1 micron, preferably 0.5 micron, silicon-rich silicon nitride 33a and 0.2 to 1 micron, preferably 0.5 micron, silicon 33b, for example, by a process such as chemical vapor deposition. Other possible masking layers include silicon, silicon dioxide, silicon carbide, and combinations thereof.

Figure 2B:
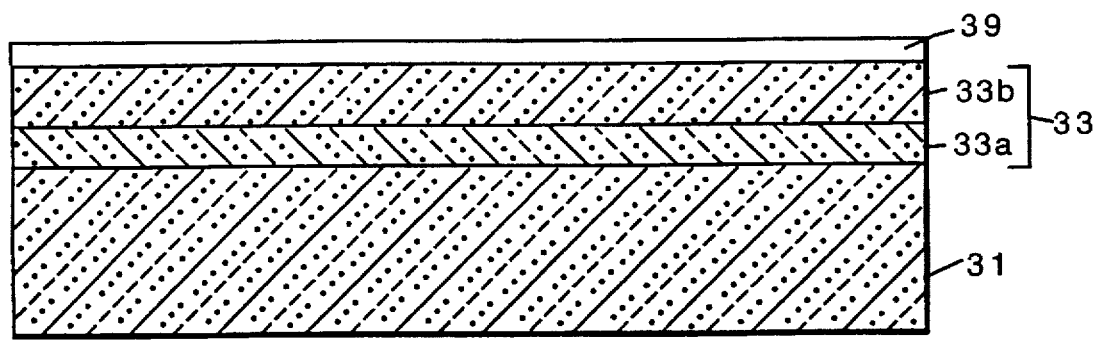
Figure 2C:
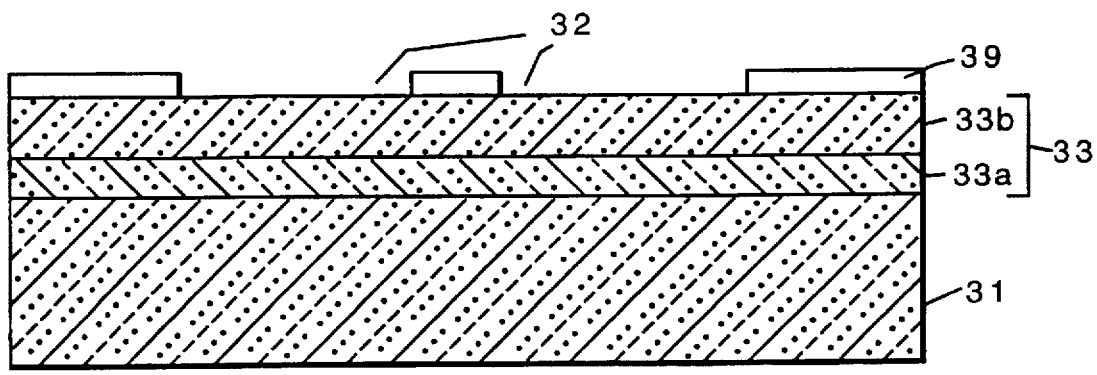

As shown in FIGS. 2B and 2C, the masking layer 33 is coated with a spin-applied photoresist 39. The resist 39 is photolithographically patterned with the desired shape 30 (FIG. 2H) of a mold cavity for a structural support member 25 (FIG. 1A) as a series of perforations 32 about 1 to 6 microns wide in the resist 39 exposing the mask 33.

Figure 2D:
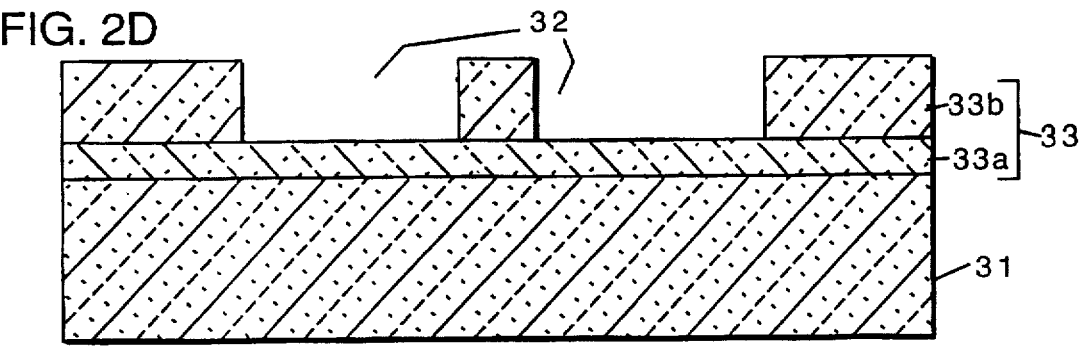
Figure 2E:
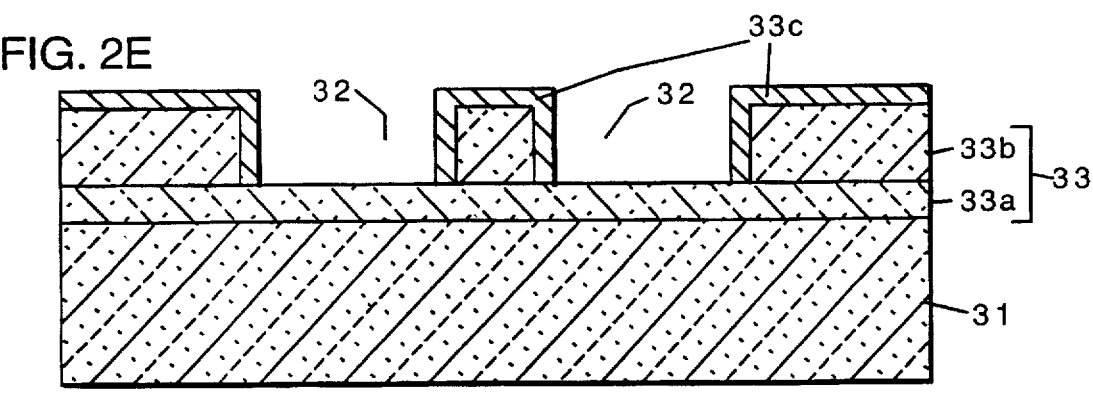
Figure 2F:
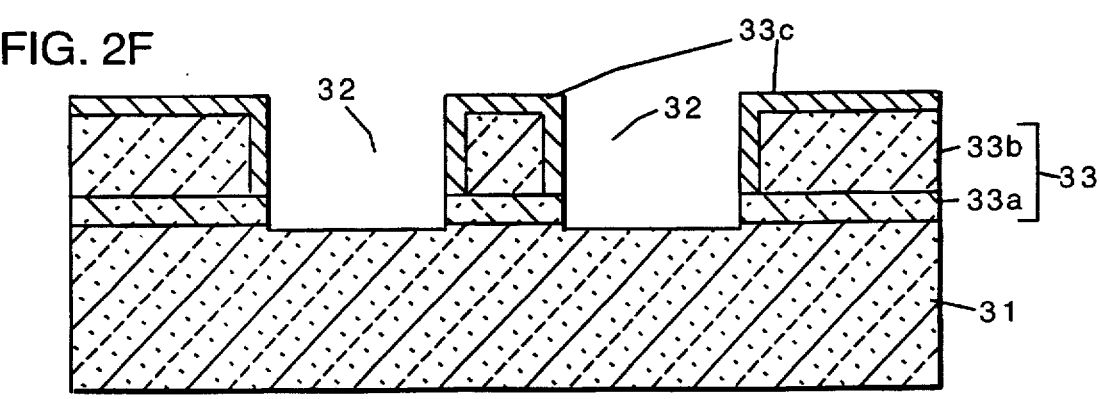

Referring to FIG. 2D, the exposed portions of the mask 33, defined by the perforations 32, are then plasma etched, extending the perforations 32 to the silicon nitride layer 33a. The photoresist 39 is removed and the wafer 31 is placed in an oxidation furnace to grow a thermal oxide layer 33c on the exposed silicon layer 33b, as shown in FIG. 2E. The wafer 31 is then plasma etched to extend the perforations 32 to the silicon wafer 31 surface. FIG. 2F shows completion of this step. The various layers 33a, 33b and 33c of differing composition of the mask 33 are used because each has the appropriate solubility characteristics required to withstand the different etching methods used at various stages of the fabrication process.

Figure 2G:
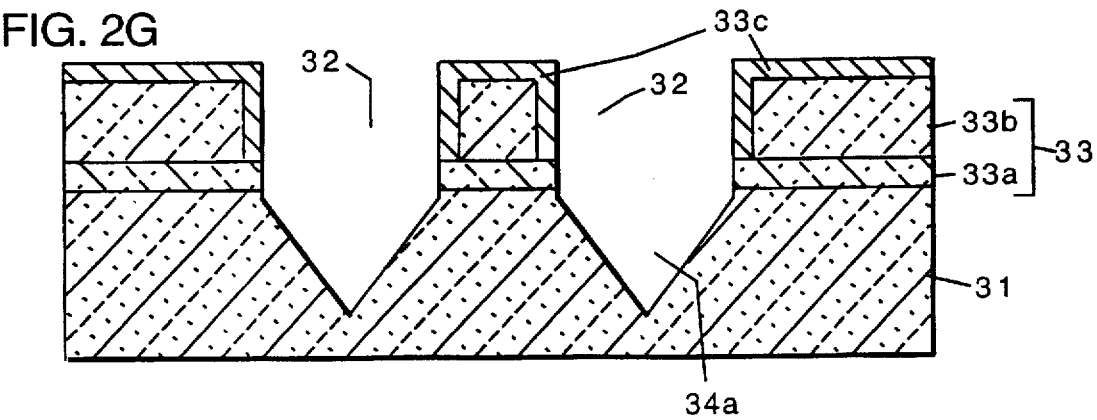
Figure 2H:
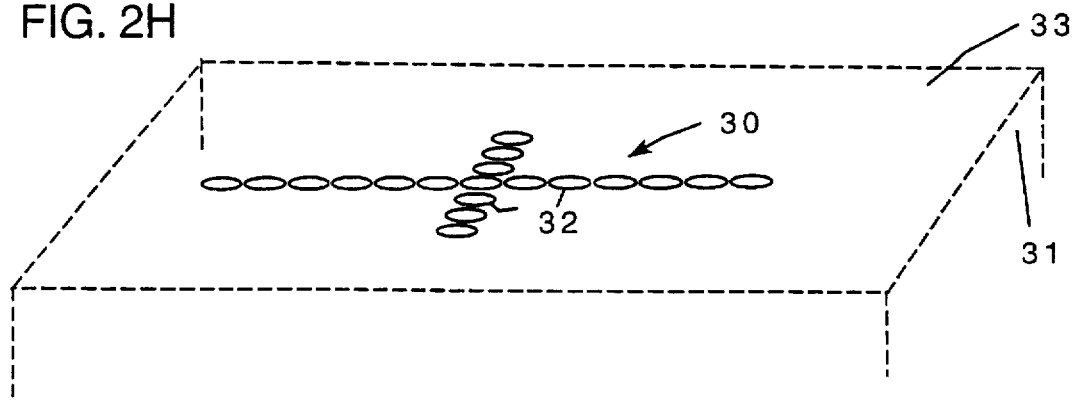

As shown in FIG. 2G, holes 34 in the wafer 31 may be started by plasma or potassium hydroxide (KOH) etching of shallow pyramidal pits 34a, whose terminal vertices are defined by the (111) planes of the silicon wafer 31. For example, the wafer 31 may be placed in a 20% aqueous solution of KOH at 20 to 80° C., preferably 60° C., for several minutes. The holes 34 are started in this manner because the pyramidal shape of the pits 34a causes the electric field of the photoelectrochemical etching step to be concentrated in the middle of the holes 34 (FIG. 2I), thereby achieving the best etching results with the least lateral etching. FIG. 2H is a perspective representation of the wafer processed to this stage.

Figure 2I:
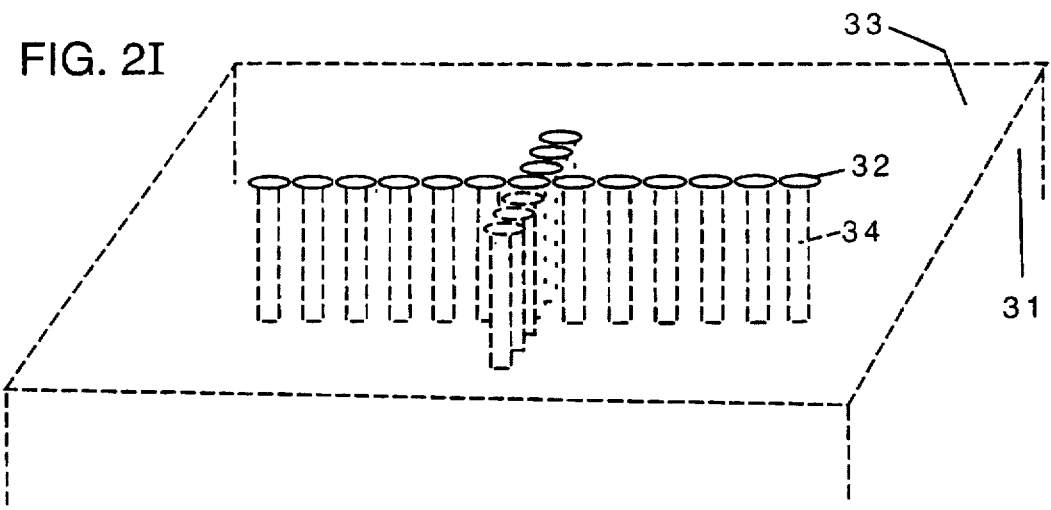

Referring to FIG. 2I, holes 34, having a width less than the desired thickness of the thin film structural member 25 to be formed in this part of the mold, are then photoelectrochemically etched in the wafer 31, extending the etched pyramidal pits 34a. The holes 34 are etched to a depth approximately equal to the desired height of the structural member 25. Hole depths, and therefore structure heights, of approximately 600 microns or more are achievable by the present method, without significant lateral etching. The wafer 31 is then thoroughly rinsed with deionized water.

Photoelectrochemical etching may be conducted as follows. Possible process parameters are 10 milliamperes per square centimeter (mA/cm$^2$) etching current, 10% hydrofluoric acid (HF) concentration, using a platinum cathode, and light being shined on the back of the wafer i.e. the side opposite the patterned side. Referring to Figure The shallow etched pyramidal pits 34a in the wafer 31 may be exposed to an aqueous solution of 3 to 10% HF with sufficient hydrogen peroxide, or other oxidizing agent, to suppress the formation of hydrogen bubbles. A platinum electrode (not shown) is located in the HF solution and a wire (not shown) is in contact with the back of the wafer 31, which is isolated from the solution. The wafer 31 is made positive with respect to the platinum electrode in the solution by about 3 volts. A light is made to shine uniformly on the back of the wafer 31. The light is passed through a filter (not shown) to eliminate all photons of wavelength greater than 8000 angstroms before impinging on the wafer 31. The brightness of the light may be adjusted to achieve the desired etch current; the greater the etch current, the greater the hole 34 diameter. Etching is stopped when the desired depth of the holes 34 is reached and the wafer 31 is thoroughly rinsed with deionized water.

Figure 2J:
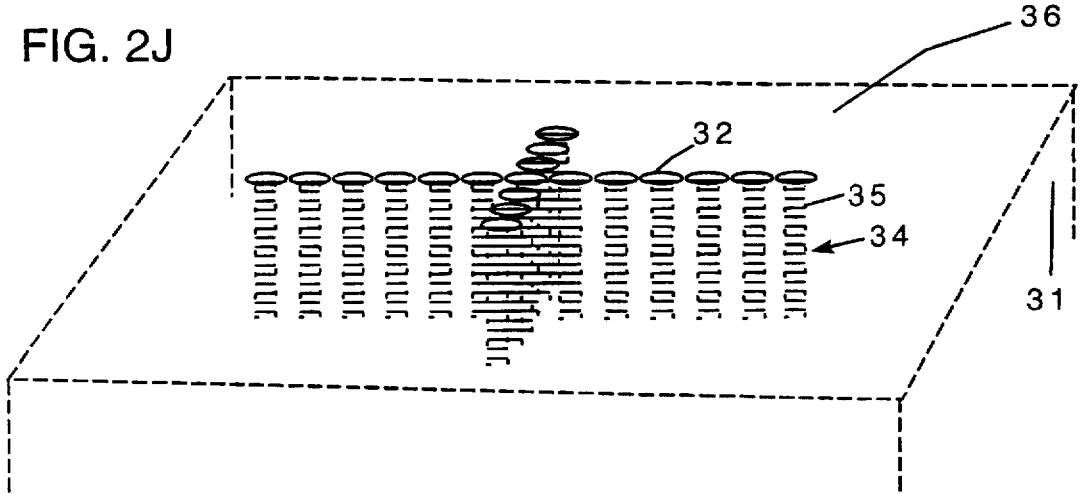
Figure 2K:
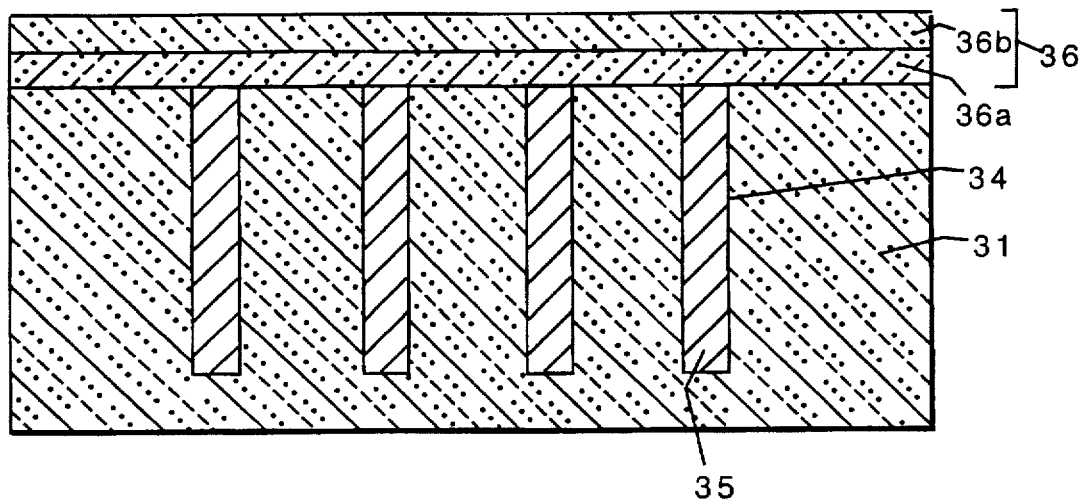
FIG. 2K is a schematic sectional view of plugged and protected holes etched in a substrate wafer.

Once the desired hole depth is reached, the holes 34 may be plugged with oxide 35, for example, by thermal oxidation of the wafer 31, and covered with a protective coating 36 of silicon over silicon nitride, as shown in FIG. 2J and 2K.

Figure 2L:
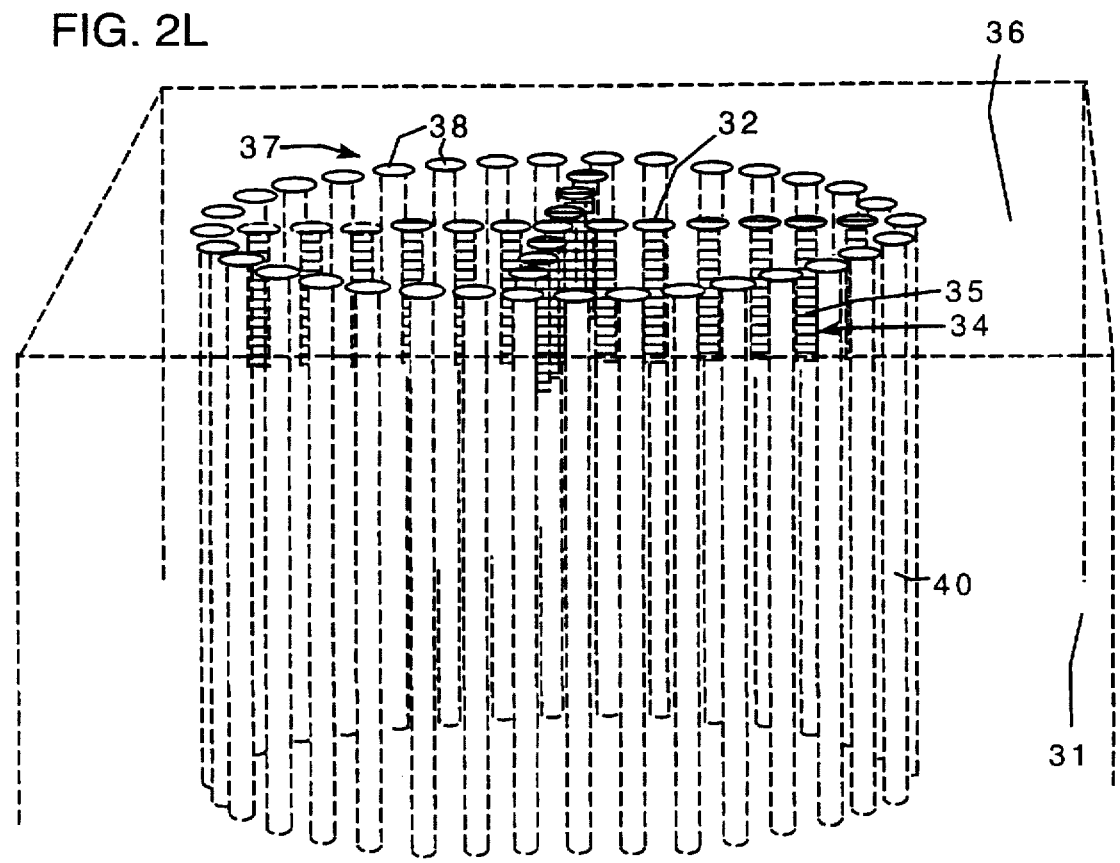

Referring to FIG. 2L, a pattern 37 for the side walls 22 may then be photolithographically patterned around the protected end face support structure holes 34 as a second series of perforations 38, according to the method described above. A second, deeper set of holes 40 are then photoelectrochemically etched according to the same procedure described above. These holes 40 will have a diameter less than the desired thickness of the side walls 22 of the capsule 20, and be etched to a depth approximately equal to the desired height of the thin film structure 46 (FIG. 2O) to be fabricated. For a containment capsule, this is preferably between about 50 and about 600 microns.

Figure 2M:
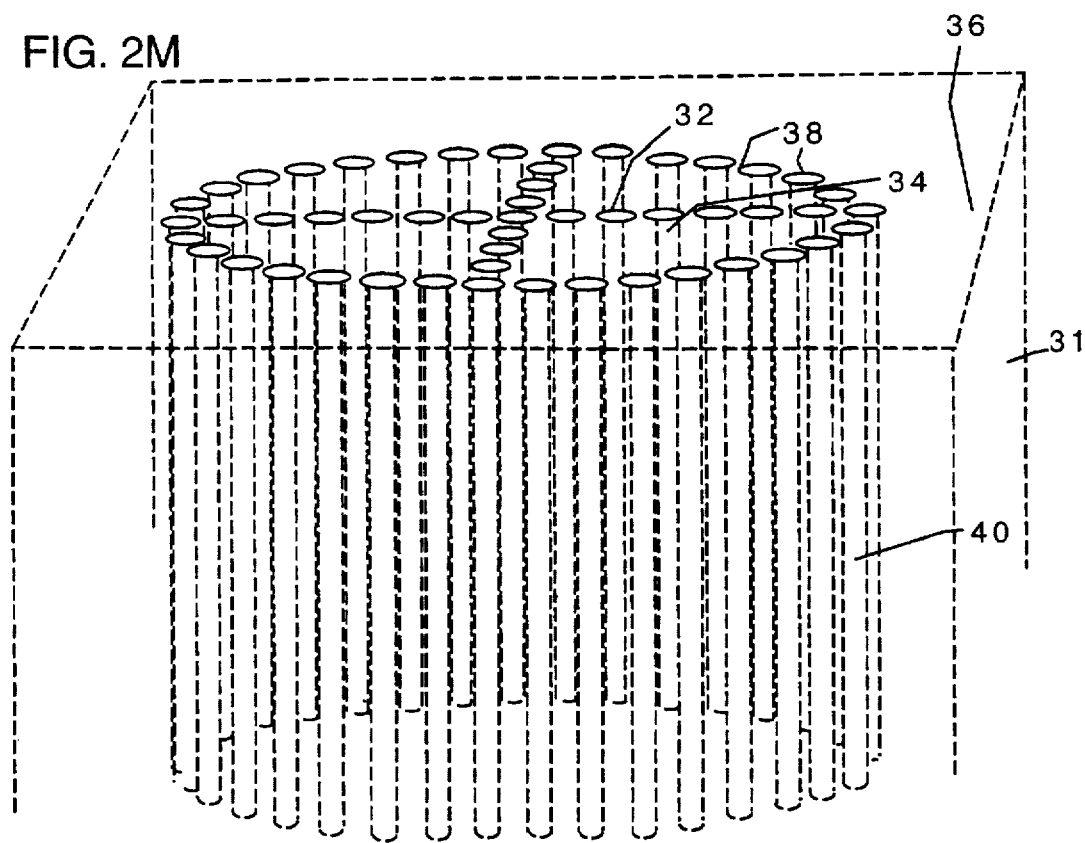

FIG. 2L shows all the holes 34 and 40 etched into the wafer 31 following the steps described above, thus defining two structural depths. In FIG. 2M, the nitride protective layer over the shallow holes 34 is removed by hydrofluoric or phosphoric acid, or plasma etch, and all the holes 34 and 40 are repeatedly and alternately oxidized, preferably thermally, and etched, preferably with 49% hydrofluoric acid, until they merge into continuous side wall trenches 42 and structural rib trenches 43, which define the mold 44 for the capsule walls 22 and support members 25. Alternately, an isotropic wet etch, for example, 65% nitric acid, 3% ammonium fluoride, and 32% water, can be used.

The roughness of the mold 44 surfaces may be smoothed by placing the mold wafer 31 in a tube furnace for wet oxidation at 1100° C. for 2.5 hours to grow 1 micron of oxide. This is then completely removed by a 49% hydrofluoric acid etch. Alternatively, smoothing may be accomplished by timed isotropic etch with a solution of 65% nitric acid, 3% ammonium fluoride, and 32% deionized water at room temperature.

Molds may be formed by the techniques herein described for structures of varying shape and complexity. For instance, depending on the structural requirements of the structure formed, the side wall and support structures may be reinforced. For example, a mold may be formed as described above to produce a structure having side walls 22 with reinforcements 23 like those shown in FIG. 2R. In such a case, the pattern for the mold would consist of two concentric circles bridged at regular intervals. Holes would be etched and trenches formed according to the method described above in relation to FIGS. 2A to 2N.

Figure 2N:
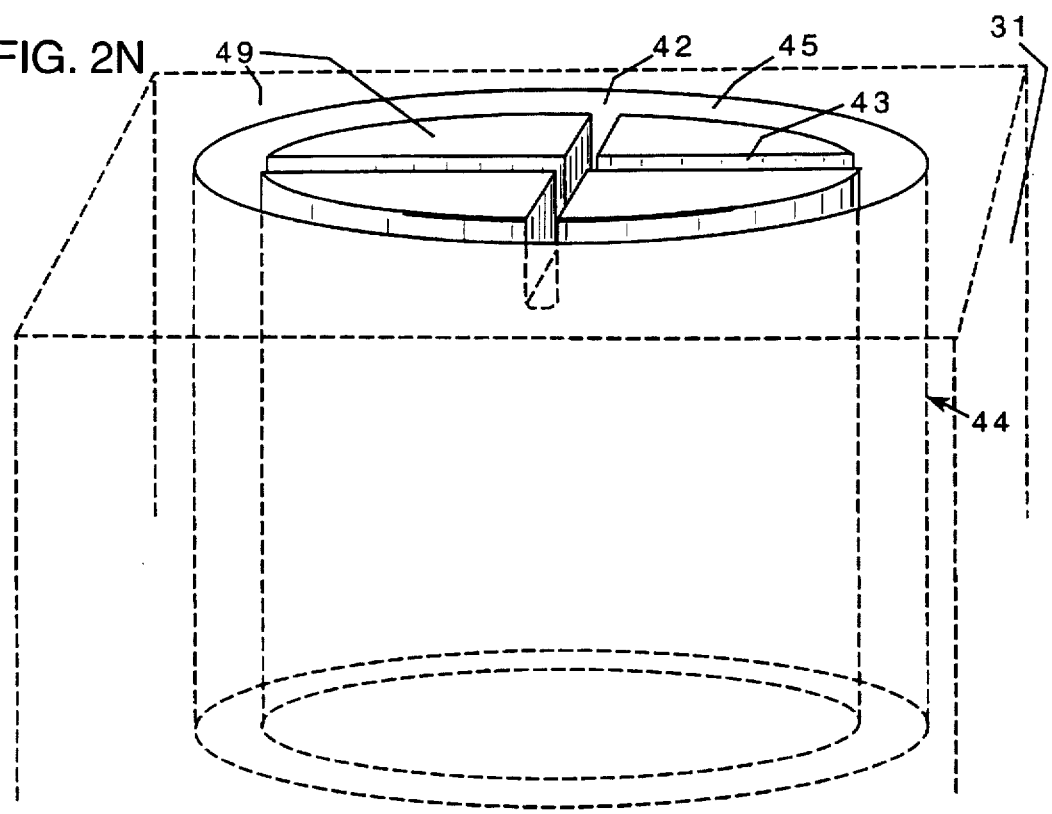
Figure 20:
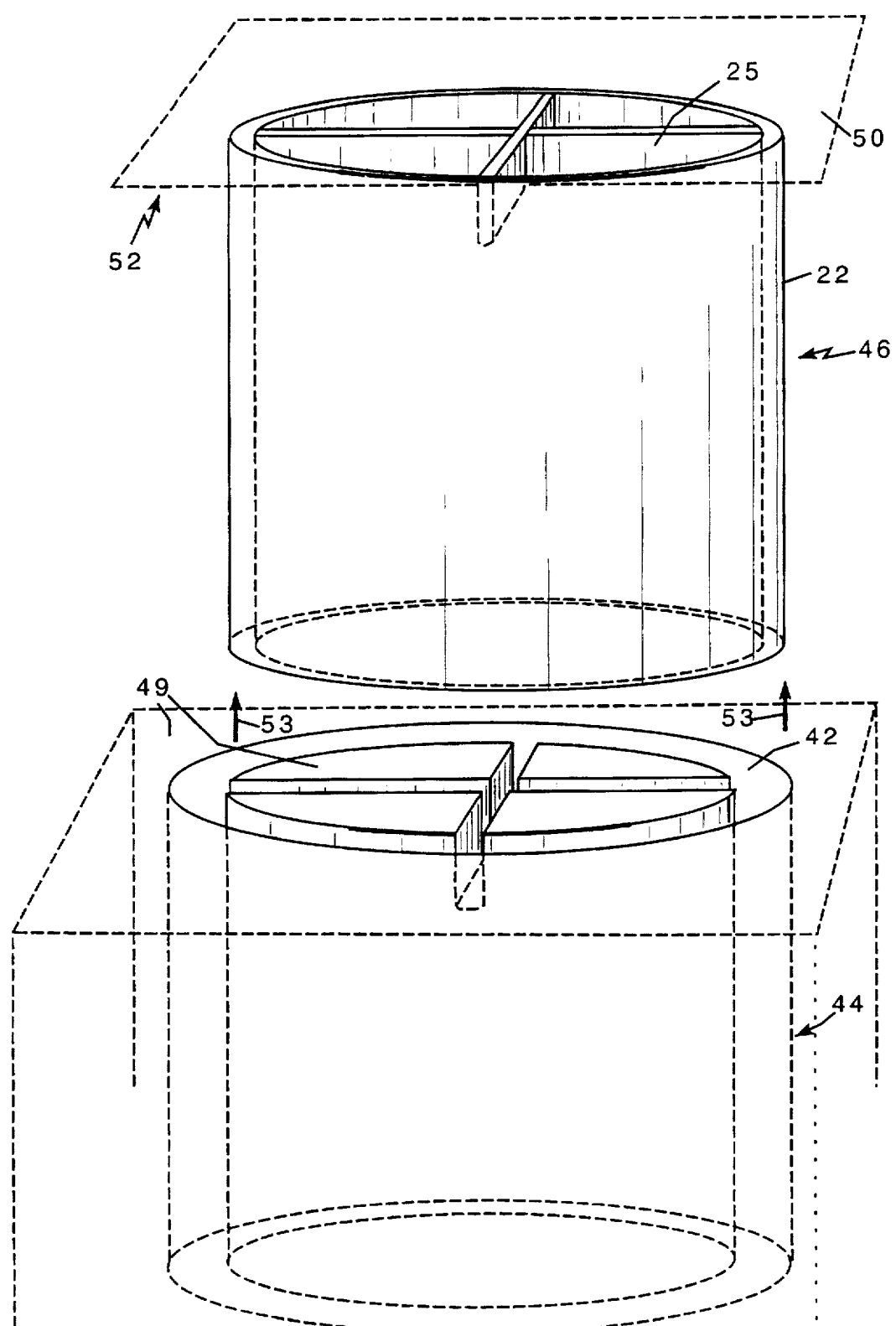

Referring to FIG. 2N, following completion of the mold 44, the surface of the mold wafer 31 may be lapped and polished in order to provide a flat surface amenable to subsequent processing. Lapping and polishing may be achieved by applying a slurry of 0.3 micron deagglomerated alpha alumina in glycerin.

Thereafter, the mold 44 is lined with a sacrificial layer 45. Typically, a layer of silicon dioxide is used wherever a sacrificial material is needed. Several methods may be used to create sacrificial oxide layers.

Thermal oxidation of the wafer 31 may be used. However, this consumes silicon from the mold 44, and should only be done once for smoothing the etched surface, as described above.

Therefore, a preferred method uses chemical vapor deposited (CVD) polysilicon at 580° C. and 65 Å per minute, followed by complete conversion of this layer to oxide by wet thermal oxidation at 1100° C. This method produces a very conformal coating, that is, one of uniform thickness regardless of the topography of the substrate, and does not consume the mold 44. The CVD polysilicon may be selectively doped by phosphine during the deposition to create conductive regions in the structure formed.

Other possible methods use CVD phosphosilicate glass (PSG) at 450° C., 140 Å per minute, and 8% phosphorous in the film, or CVD undoped oxide at 450° C. PSG provides a relatively fast etching layer (up to 20 microns ($\mu$m) per minute in 49% hydrofluoric acid (HF). Combinations of these methods can also be used.

The sacrificial layer 45 is needed during fabrication to prevent structural layers from being deposited directly in contact with and bonding to the mold 44. The final step of fabrication is to etch away this material to detach the finished structure from the mold 44.

Following deposition of the sacrificial layer 45, the mold 44 is filled, preferably by chemical vapor deposition (CVD), with a suitable inorganic material that will form the structure 46. The material has two principal requirements: it must be capable of conformal deposition, that is, it must be capable of completely and uniformly filling the mold 44 without leaving any voids, regardless of the topography of the substrate; and it must be able to withstand the etch step that will be used to remove the sacrificial layer 45 from the mold 44 in order to release the structure 46. In addition, a structure 46 that is to form part of a containment capsule 20 for in vivo applications must be composed of a biologically compatible material, that is, a material that does not cause any adverse reaction when implanted in living tissue. Examples of such materials include amorphous and polycrystalline silicon, preferably CVD polysilicon, silicon nitride, and tungsten. These materials are also mechanically stronger than organic membranes, so they can be made thin enough to allow the high diffusion rates needed, while also being amenable to fabrication processes which provide well controlled pore sizes and distribution. Capsule membranes or shells composed of such materials could be as little as 100 angstroms thick and approach the performance of a living cell membrane with respect to simultaneously achieving high diffusivity with high selectivity.

The CVD filling may be done with polysilicon at 580° C. with a deposition rate of about 0.39 microns per hour, 100 standard cubic centimeters per minute (sccm) silane, at 300 millitorr.

Following the filling of the mold 44, the wafer 31 may be lapped and polished to provide a flat planar surface and then the substrate surface 49 may be selectively etched to expose the top surfaces of the structural support members 25 and side walls 22 for subsequent addition of other elements, such as porous end face 24, in the case of a containment capsule.

The structure 46 may then be released from the wafer 31. Alternatively, the structure 46 may be processed further prior to being released, as discussed below. Release may be accomplished by etching away the sacrificial oxide layer 45 with hydrofluoric acid (HF). The sacrificial oxide may be dissolved with 49% HF with surfactant, such as triton X-100 at a concentration of about 0.1% in complete darkness. The surfactant is necessary to prevent the hydrophobic surfaces of the released silicon structures from sticking together to minimize contact with the aqueous solution. Enough surfactant must be present to form a monolayer on all surfaces. The darkness is a precaution against photon induced etching of silicon.

Figure 2P:
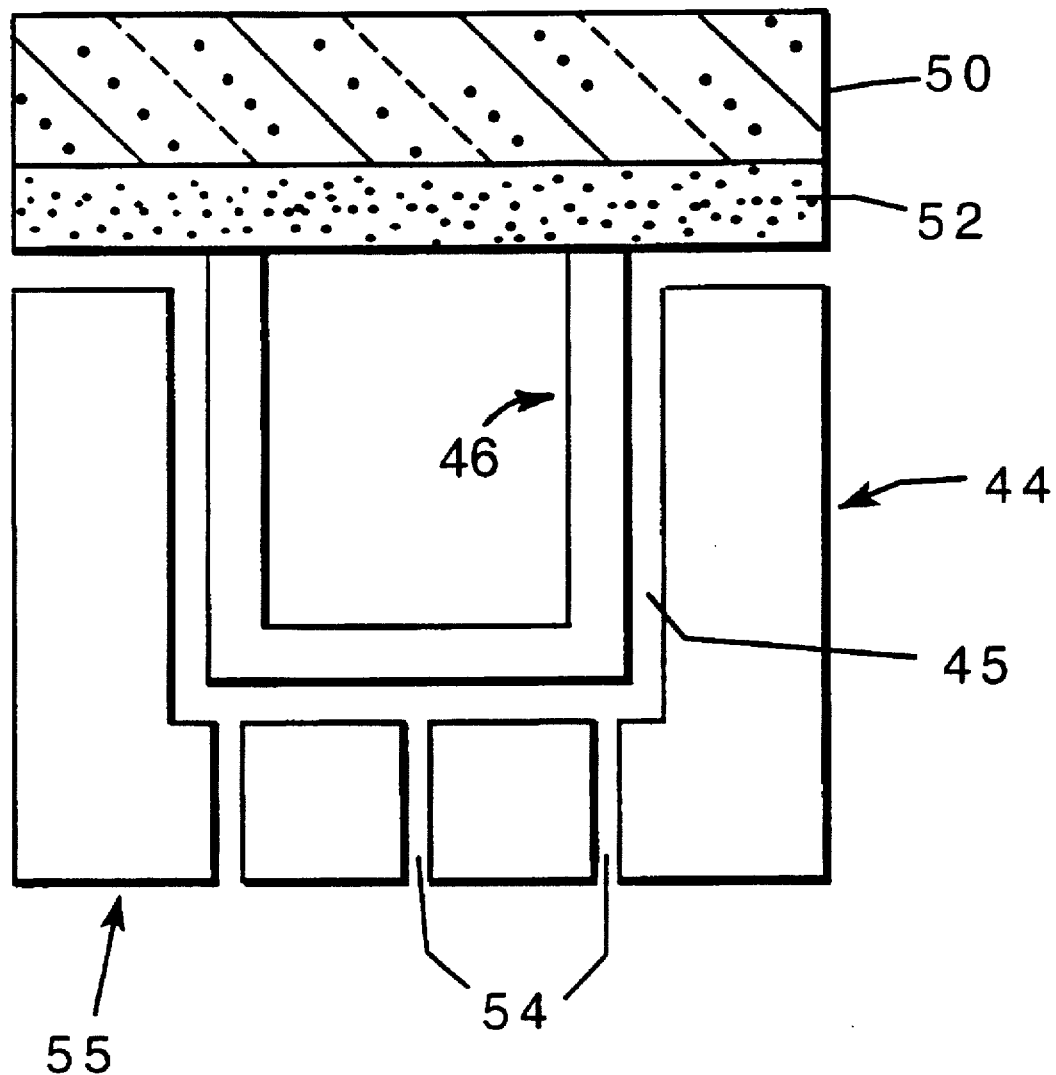
FIG. 2P is a schematic sectional view of photoelectrochemically etched long, small diameter passageways in the back of the mold wafer useful for hydraulic ejection of the finished structure from the mold.

Referring to FIGS. 2O and 2P, if the wafer 31 was lapped and polished before etching of the sacrificial layer 45, the structure 46 extends beyond the top surface 49 of the mold 44. A flat wafer 50 with a sticky surface 52, such as a coating of wax or hydrophobic double-sided tape, may be used to lift the structure 46 from the mold 44, as represented by arrows 53. FIG. 2O shows the removal of structure 46 from the mold 44 according to this method, after the sacrificial layer 45 coating the mold 44 has been etched.

Figure 4A:
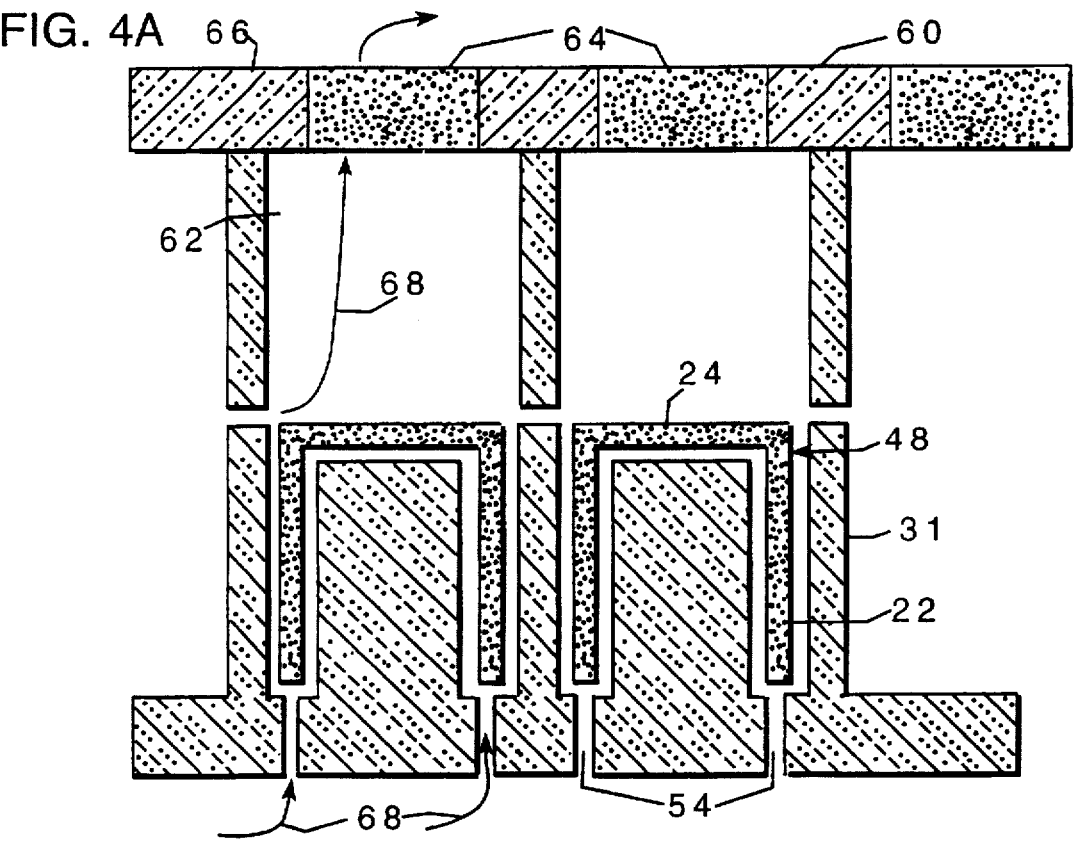
FIGS. 4A–4C and 4E–4G are schematic, sectional views of later stages in the fabrication process of a capsule according to the present invention.
Figure 4B:
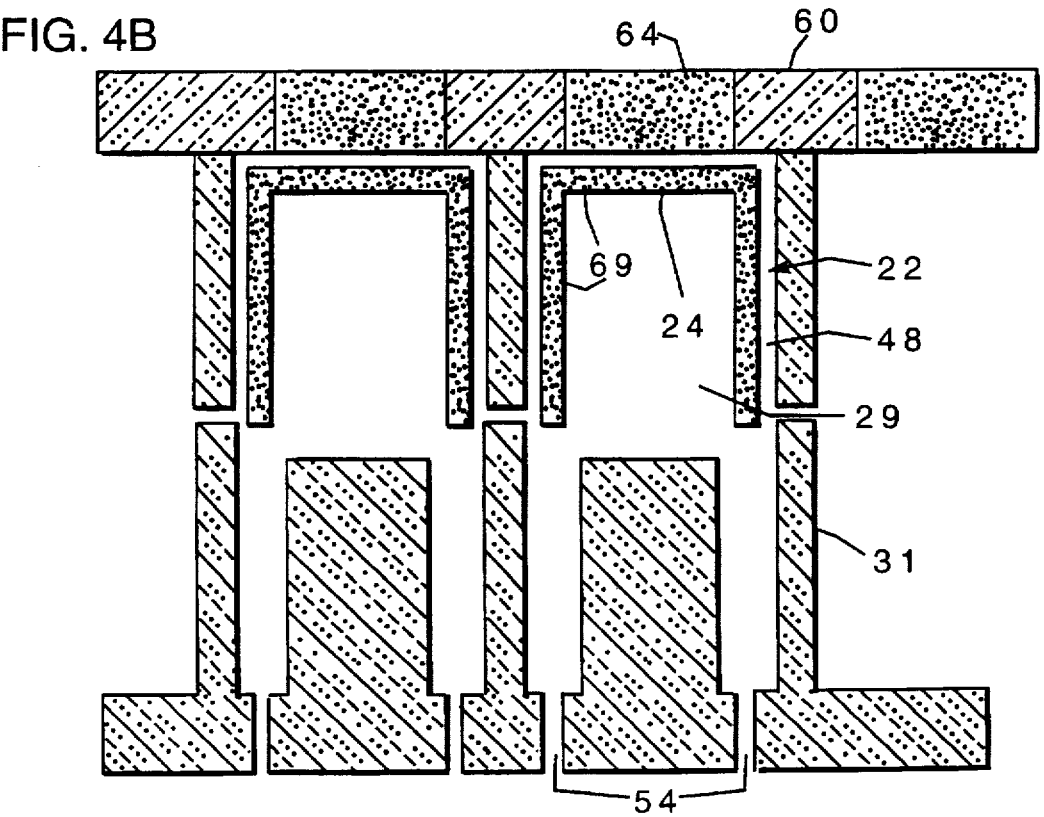

Another method for removal of the completed structure 46 from the mold 44 is shown in FIG. 2P. If the substrate 31 for the mold 44 is n-type (100) polysilicon, long small diameter passageways 54 leading from the back 55 and through the thickness of the mold 44 may be photoelectrochemically etched by methods known in the art and described above. These passageways may be used to connect the bottom of the mold 44 to a source of hydraulic pressure for ejection of the structures 46 once the sacrificial oxide layer 45 is removed. The preferred working fluid is deionized water with 0.1% surfactant such as Triton-X100, available from Sigma Chemical Co., 3500 De Kalb, St. Louis, Mo. 63118. Alternatively, the structure 46 fabricated in mold 44 in accordance with the present invention, may be ejected directly into receiving cavities 62 that have been etched into a second wafer 60, as shown in FIGS. 4A and 4B for a partially completed capsule 48, and discussed in more detail below.

Figure 2Q:
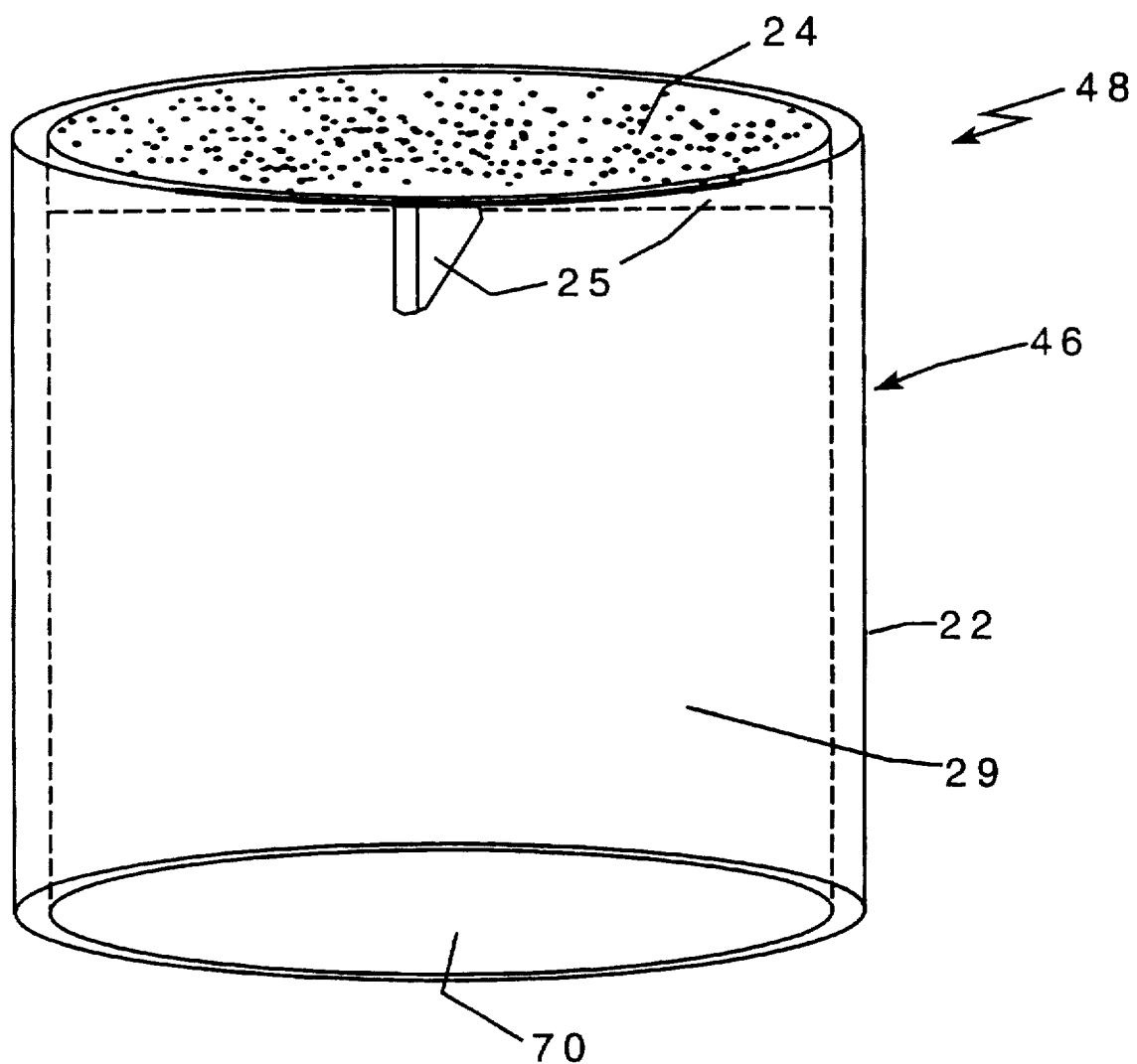
Figure 2R:
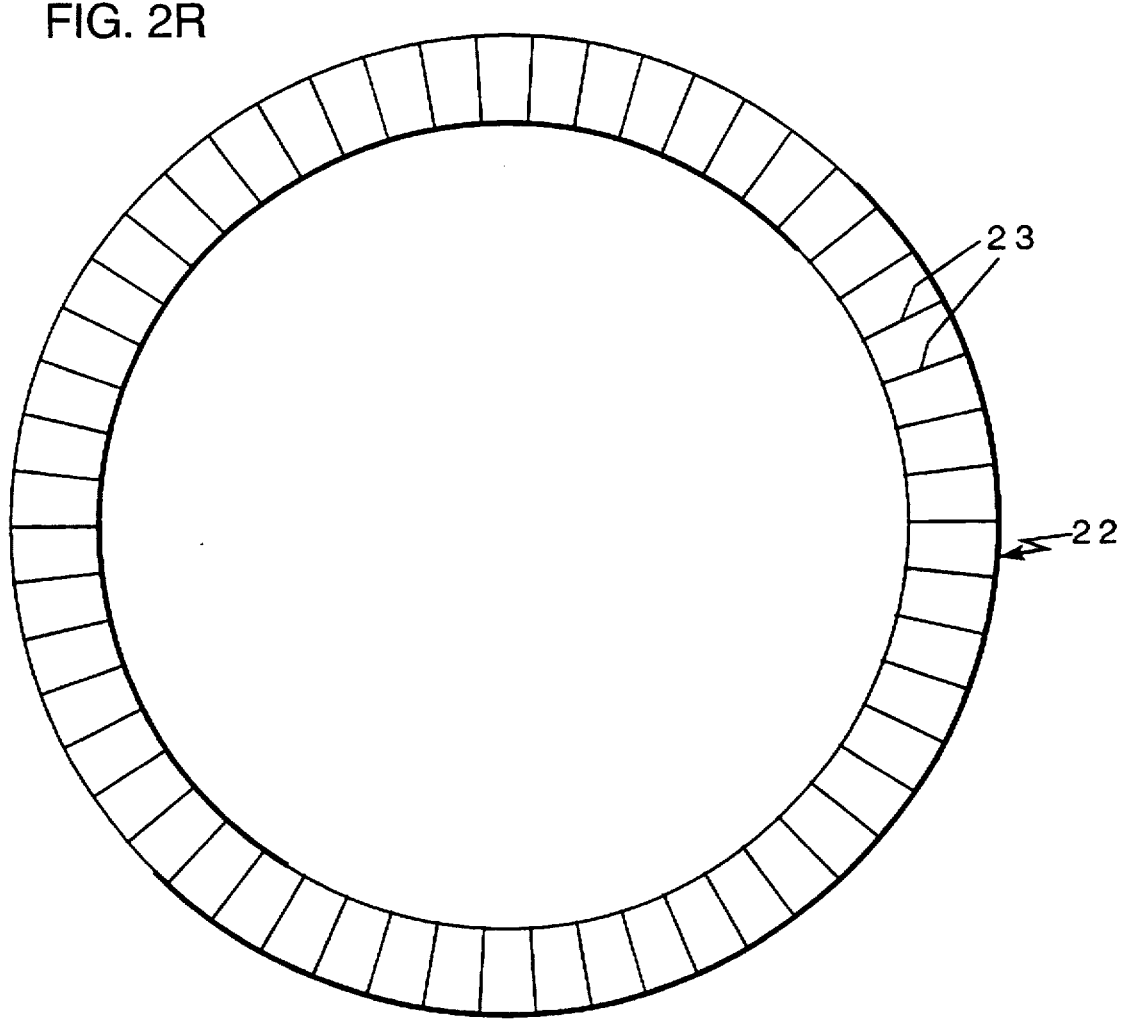
FIG. 2R is a schematic sectional view of a reinforced side wall structure of a capsule according to the present invention.

If the structure 46 is to form part of a more complex structure, such as a containment capsule 20, it may be processed further prior to removal from the mold 44. In FIG. 2Q, a partially completed capsule 48 is shown comprising structure 46 with the addition of a microfabricated filter end face 24, such as is described in applicants' above identified patent application entitled MICROFABRICATED PARTICLE FILTER, Ser. No. 08/207,457, now U.S. Pat. No. 5,651,900. To complete the capsule 20, a second filter is attached to the remaining open end 70.

Figure 3A:
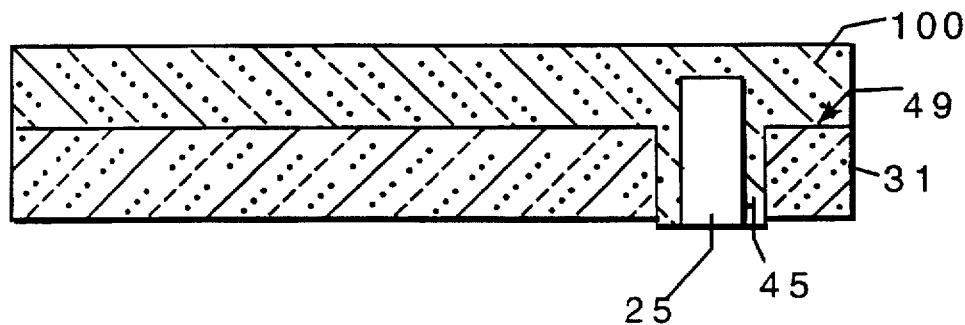
FIGS. 3A–3H are schematic sectional views of the fabrication steps of a filter end face according to the present invention.
Figure 3B:
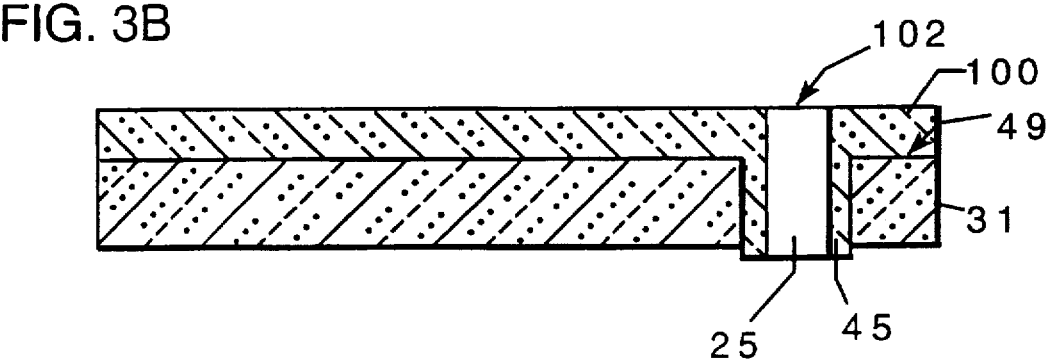

By way of example, a filter may be fabricated on the exposed portions of the structure 46 and support member 25 as follows, as shown in FIGS. 3A to 3H. A sacrificial layer 100 is grown on top surface 49 of the mold substrate 31 to allow the finished filter to be separated from the substrate 31, as shown in FIG. 3A. By way of example, a 2 micron thick film of silicon dioxide may be deposited by chemical vapor deposition at 450° C. The exposed surface 49 of the substrate is thus coated with a sacrificial layer 100. The sacrificial layer 100 may then be etched back until the surfaces 102 of the structural members 25 and side walls (not shown) are exposed, as shown in FIG. 3B.

Figure 3C:
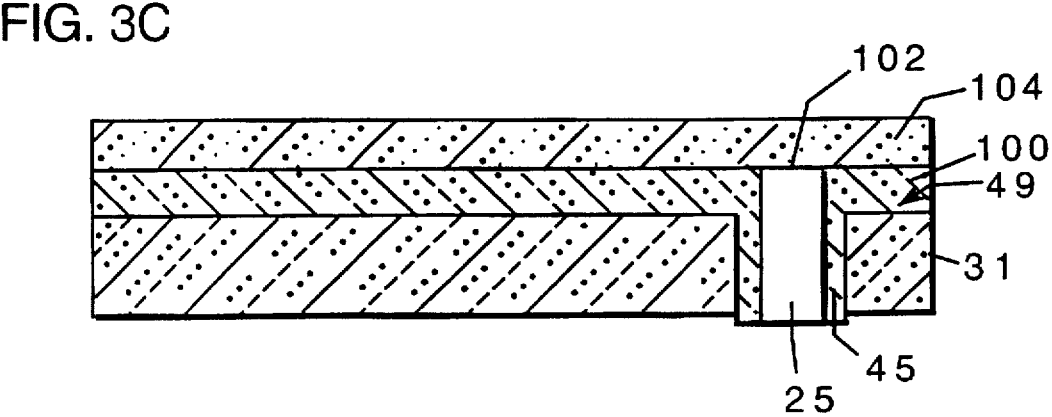
Figure 3D:
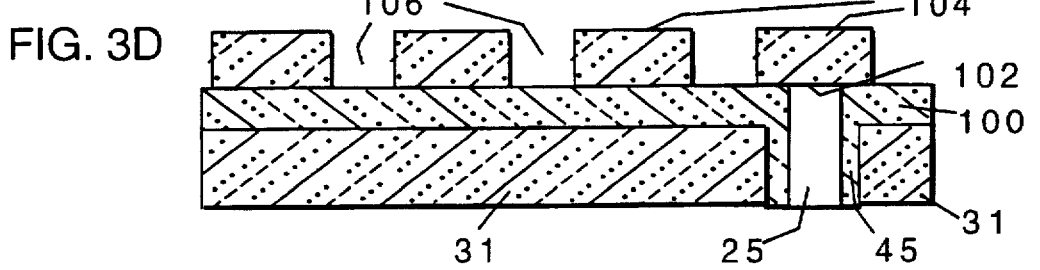

As shown in FIG. 3C, a first thin film structural layer 104 can then be deposited over sacrificial layer 100 and surfaces 102 and patterned, as shown in FIG. 3D, by photolithography and etching to form apertures 106. Layer 104 may be a 2 micron thick amorphous silicon film grown by CVD. Where layer 104 contacts surfaces 102 it bonds, thus becoming part of structure 46.

Figure 3E:
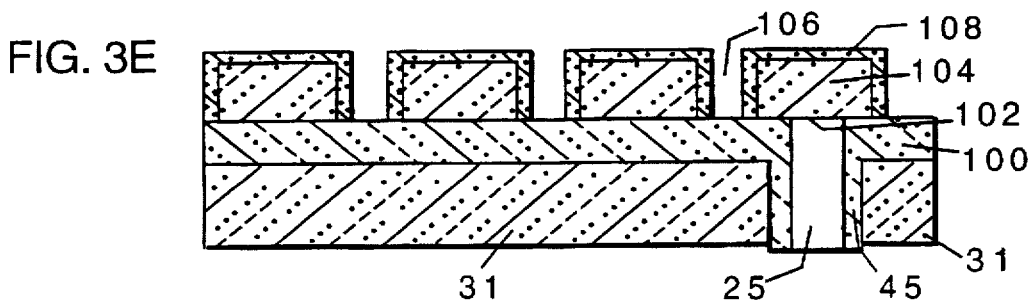

As shown in FIG. 3E, a thin film 108 is then grown on film 104 to provide a pore sacrificial layer for defining the pore shapes. The thickness of this film is equal to the desired width of the pores in the filter, typically 50 to 3000 angstroms. Film 108 may be silicon dioxide grown by oxidizing film 104. It is patterned photolithographically and etched to expose the underlying structural layer 104 in the selected areas 110 (see FIG. 3K). This is where first structural layer 104 will be bonded to a second structural layer 112 which will provide the walls of the pores that are not provided by film 104.

Figure 3F:
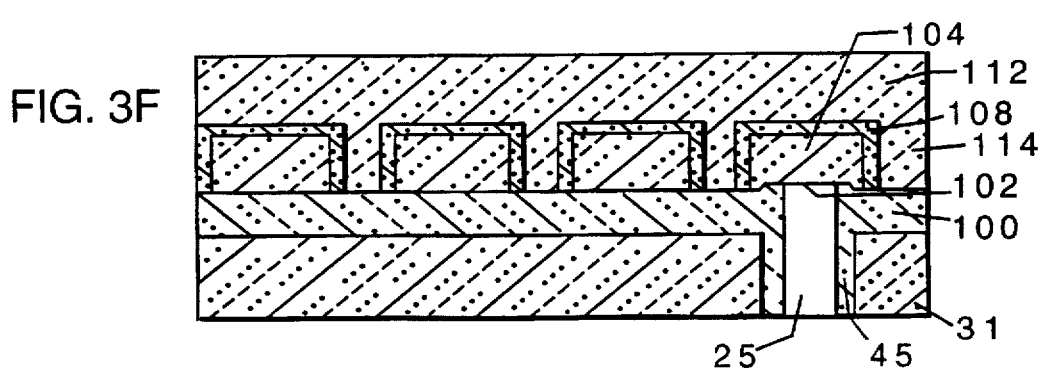
Figure 3G:
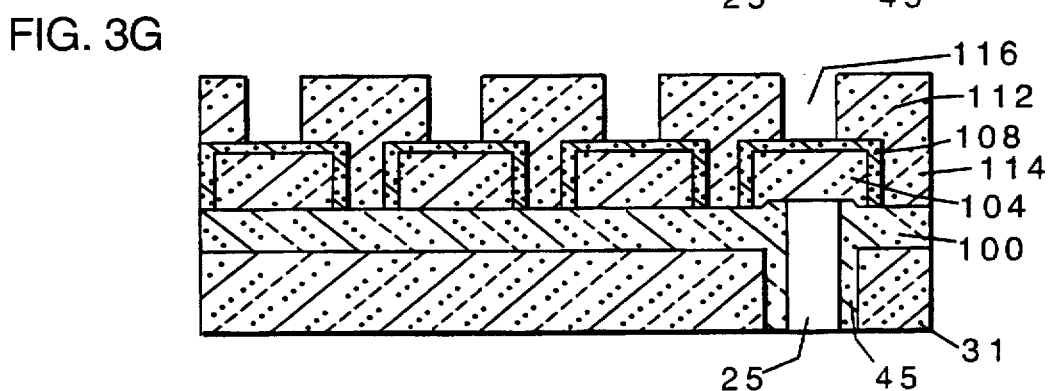

Second structural layer 112 is then deposited, as shown in FIG. 3F. Like the first structural layer, the second structural layer may be a 2 micron thick film of silicon grown by CVD. Portions 114 of this layer fill the apertures 106 of film 104. Film 112 is then photolithographically patterned and etched to form apertures 116 that fit completely above unetched portions of first structural layer 104, resulting in the structure of FIG. 3G.

Figure 3H:
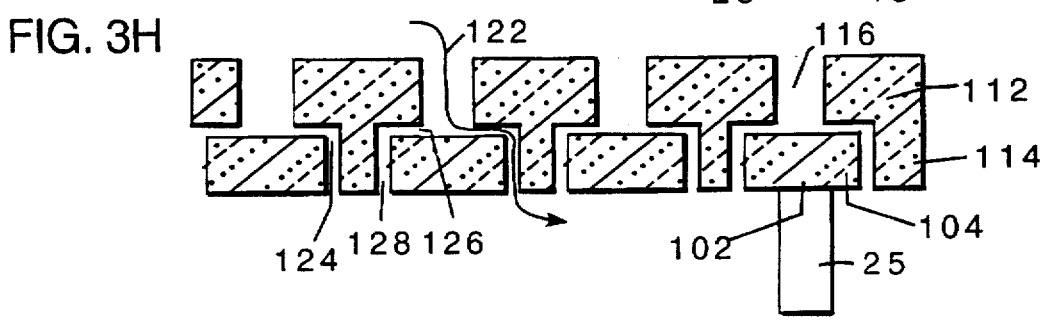

To obtain the filter end face 24 of FIG. 3H, the sacrificial layers 100 and 108 may be etched using a process that does not etch the structural layers 104 and 112, as discussed above. For this embodiment, the sacrificial layers are again made of silicon dioxide and 25 may be etched using hydrofluoric acid. Arrow 122 in FIG. 3H shows the bent path that must be traveled to pass through the pores 124 of the resulting filter 24. The width of the pores may be about 15 angstroms or larger. The length of the pores may be as low as one micron if apertures 126 and 128 are close to each other and the first structural layer is sufficiently thin.

Figure 3I:
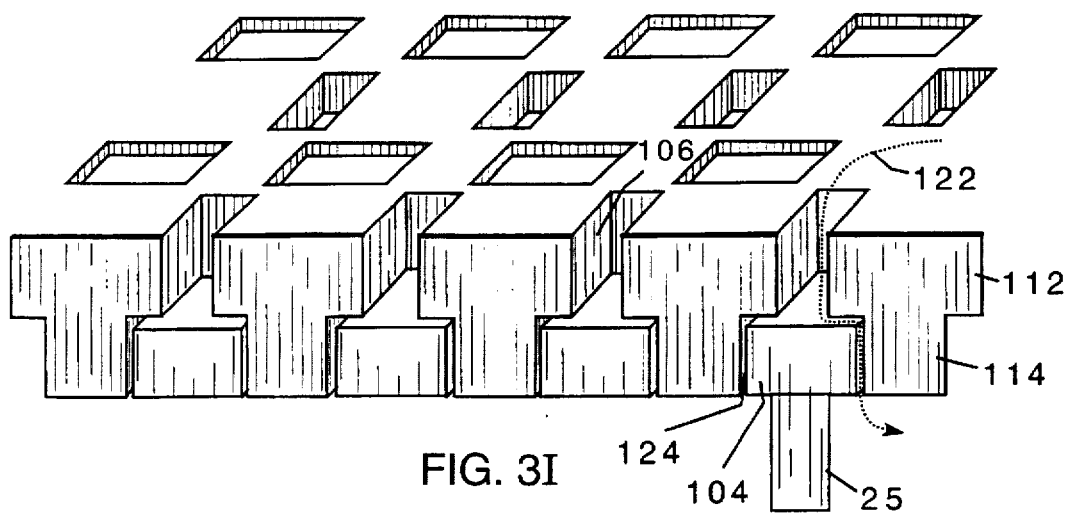
FIG. 3I shows a broken away perspective view of a completed filter end face attached to the structural support member and tops of the capsule side walls (not shown) of the present invention.
Figure 3J:
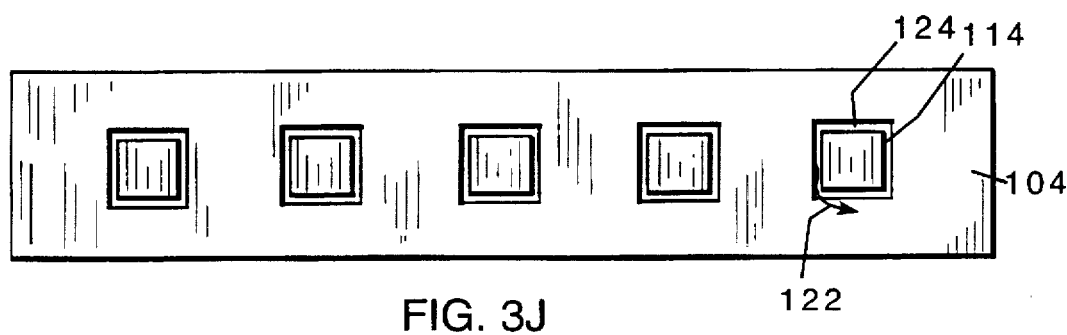
FIG. 3J shows the bottom, that is, the view from inside the capsule, of a filter end face according to the present invention.
Figure 3K:
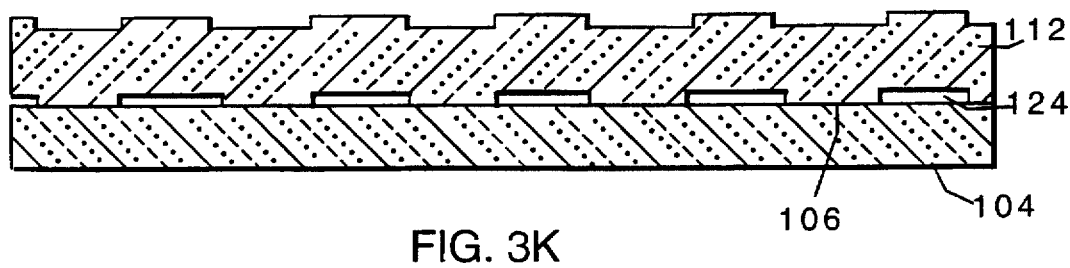
FIG. 3K shows a cross section along line A—A of FIG. 3I showing the connections between the two structural layers which form the filter end face according to the present invention.

In the embodiment of FIG. 3H, the second structural layer 112 was anchored to the first structural layer 104 by providing pore sacrificial layer 35 anchoring holes 110 (FIG. 3K). This exposes the top surface of first structural layer 104 before deposition of second structural layer 112, as shown in FIG. 3F. Many variations of this anchoring scheme are possible without departing from the scope of the present invention. Such alternative schemes may be used to optimize the bonding of different materials used as the structural layers.

FIG. 3I shows a broken away perspective view of the completed filter end face 24 attached to the structural support member 25 and tops of the side walls (not shown). FIG. 3J shows the bottom, that is, the view from inside the capsule 20, of filter end face 24. FIG. 3K shows a cross section along line A—A of FIG. 3I showing the connections between layers 104 and 112.

After etching of the sacrificial layer 45, the outer surface of the structure 46 may be treated with an organic layer 89 that cells in a host organism will not adhere to, such as a perfluorinated polyether.

FIG. 4A shows a transfer wafer 60 with a plurality of cavities 62 sized to receive the partially formed capsules 48. Each cavity 62 has a porous region 64 in its base 66 to allow fluid to flow through. This porous region 64 plays a role in filling the partially formed capsules 48, as well as getting and keeping them in the cavities 62, as is described below.

A partially formed capsule 48 is transferred from the mold 44 in the substrate wafer 31 to the cavity 62 of the transfer wafer 60, for example, by hydraulic pressure, according to the method described above in relation to FIG. 2P, applied as shown by arrows 68. Alignment of the wafers may be achieved by using a mechanical fixturing jig (not shown). Hydraulic pressure may be supplied by a syringe pump.

FIG. 4B shows the mold and transfer wafers 31 and 60, respectively, after the transfer of the partially formed capsules 48 is complete. The mold wafer 31 may now be removed and used to mold new side wall structures 46.

At this point, the interior of the side wall structure 46 and end face 24 may be treated with an organic layer 69 to which donor cells 28 will adhere, as known to those skilled in the art of cell culture. Such organic layers include may include fibrinogen, fibronectin, or laminin.

Figure 4C:
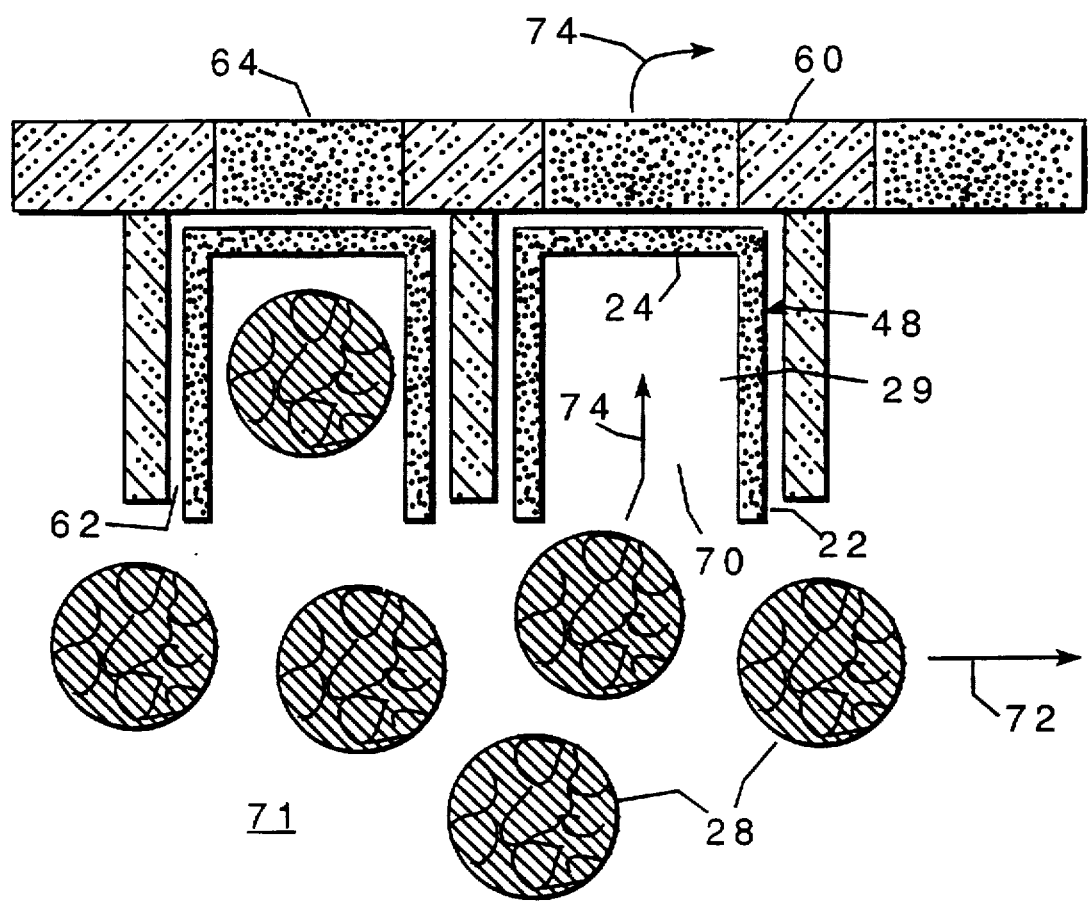
Figure 4D:
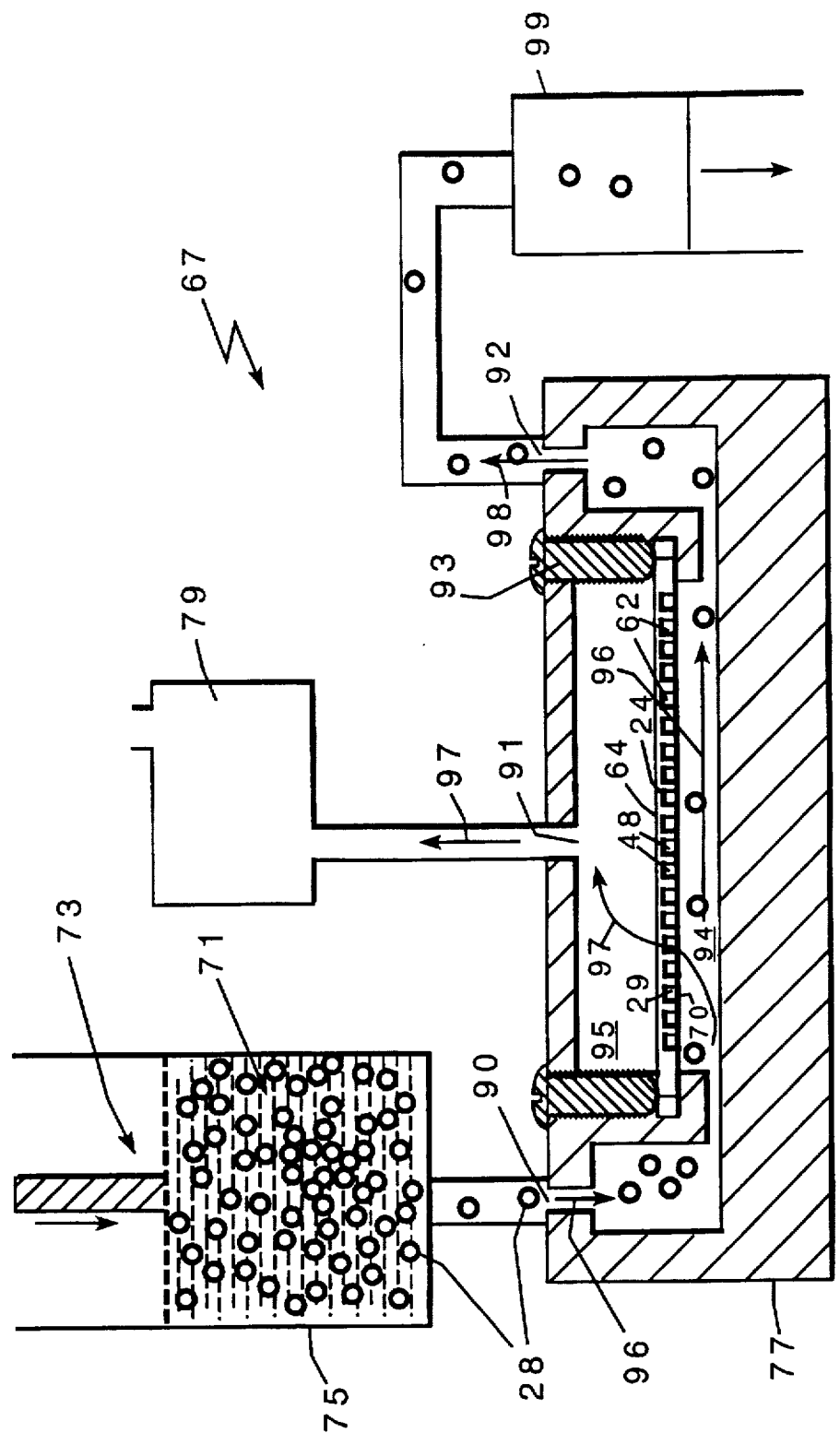
FIG. 4D is a schematic sectional view of an apparatus for filling capsules according to the present invention.

Referring to FIGS. 4C and 4D, a method and apparatus for filling the partial capsules 48 is shown, as described below. Once the mold wafer 31 has been removed, the transfer wafer 60 bearing the partially completed capsules 48 may be placed and secured in a filling apparatus 67 (FIG. 4D). The apparatus 67 may consist of a hollow housing 77 having a plurality of fluid access ports 90, 91 and 92 and means 93, such as clamps or screws, for securing the transfer wafer 60 within the hollow housing 77. Once the transfer wafer 60 is secured, the housing 77 is effectively divided into two zones 94 and 95 on either side of the wafer.

A pump 73, which may be a syringe pump, having a reservoir 75 may be connected by one of the fluid access ports 90 to zone 94 adjacent to the open ends 70 of the partially completed capsules 48 in the transfer wafer 60. A second pump 79 may be connected by a second fluid access port 91 to zone 95 adjacent to the base 66 of the transfer wafer 60.

A solution 71 containing for instance, islets of Langerhans 28, may be placed in the reservoir 75 supplied to zone 94 by a fluid flow or stream, as shown by arrows 96, generated by a syringe pump 73. The second pump 79 can generate a fluid flow or stream, as shown by arrows 97, from the first zone 94 to the second zone 95 through the partially completed capsules 48 and transfer wafer 60. In this way, the islets 28 are drawn into the partially completed capsules 48. The remaining solution 71 exits the housing 77 by port 92, as shown by arrow 98, and may be collected in receptacle 99.

Figure 4E:
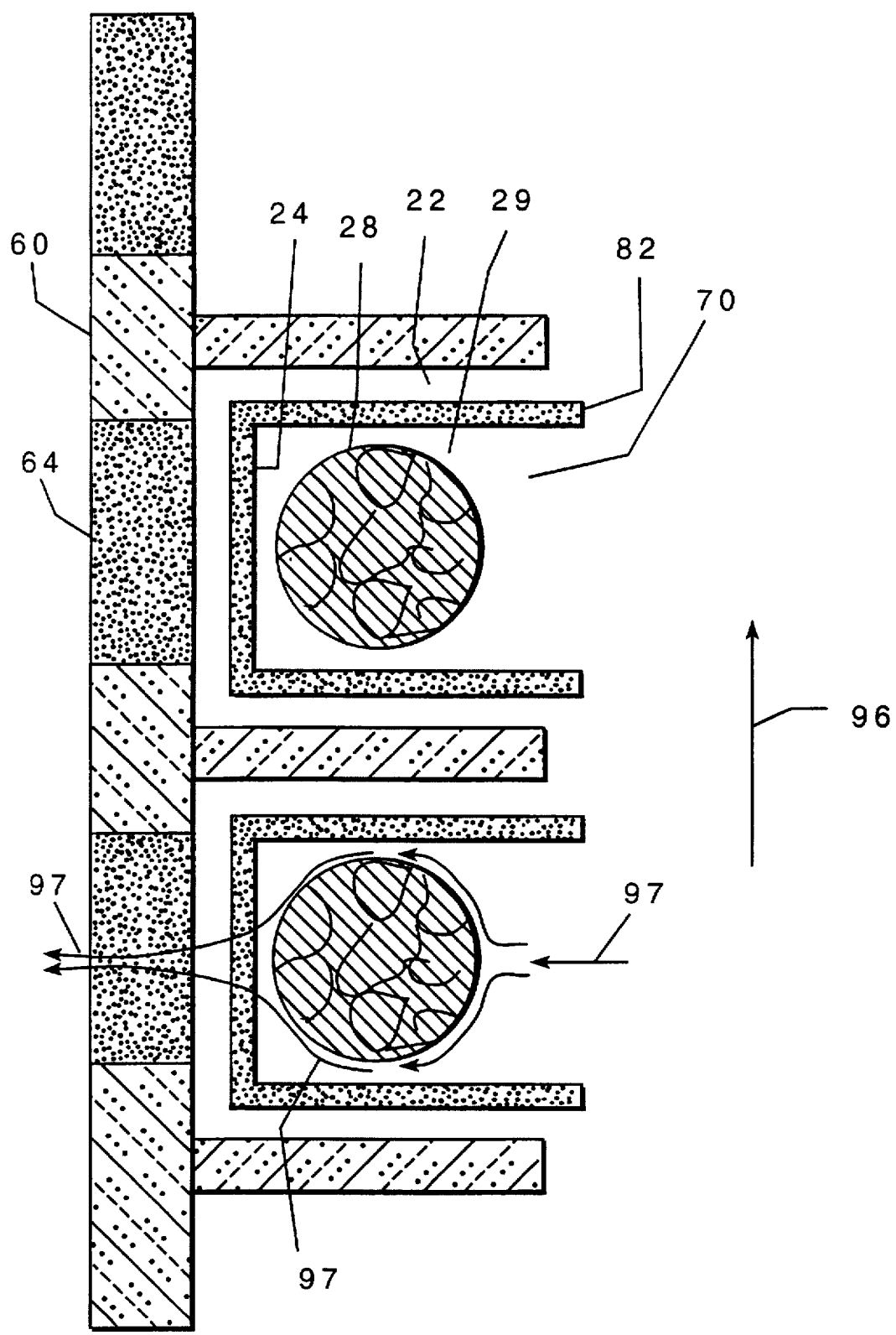

This process is continued until there is a 99.9% probability that the partial capsules 48 are filled, as shown in FIG. 4E. At this point, the supply of islets 28 to flow 96 is removed. Islet free flow 96 and flow 97 through the partial capsules 48 are maintained so that the islets 28 in the lumens 29 of the partial capsules 48 remain, while any additional islets 28 are removed from the open ends 70 of the partial capsules 48.

Figure 4F:
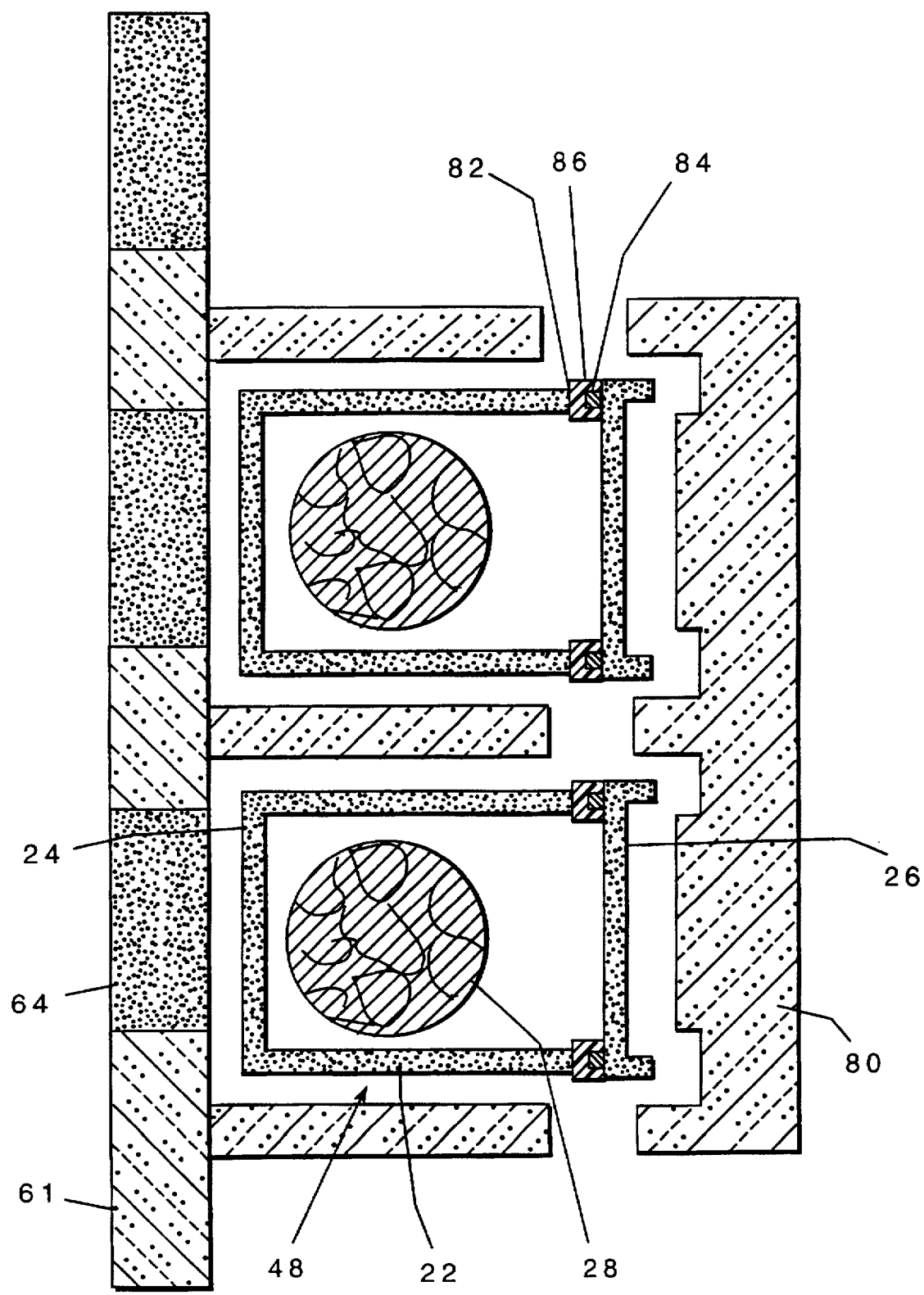

Referring to FIG. 4F, a cap wafer 80 bearing end faces 26, also formed according to the methods of applicants' above identified patent application Ser. No. 08/207,457, and as described above with respect to end faces 24, is shown. The cap wafer 80, is aligned with the positions of the partial capsules 48 on the transfer wafer 60, for example, using a mechanical fixturing jig (not shown). The cap wafer 80 is then brought into contact with the ends 82 of the side walls 22 defining the open ends 70 of the partial capsules 48, for example, by the suction pressure of flow 74. The end faces 26 also may include, at points opposite the side wall ends 82, a composition 84 capable of heating, such as tungsten or doped polysilicon. The composition 84 is covered with a sealant 86, such as polyethylene.

When the end cap wafer 80 is in position, the heating composition 84 is activated, for instance, by radio frequency or by direct current Ohmic heating, to heat the sealant 86 to a temperature sufficient to melt it, without harming the biological component contained in the capsule 20 lumen 29. The sealant 86 then bonds the end faces 26 to the side wall ends 82, thus completing the capsules 20. Alternatively, the heating composition 84 may be omitted and bonding may be accomplished with a biocompatible glue.

Figure 4G:
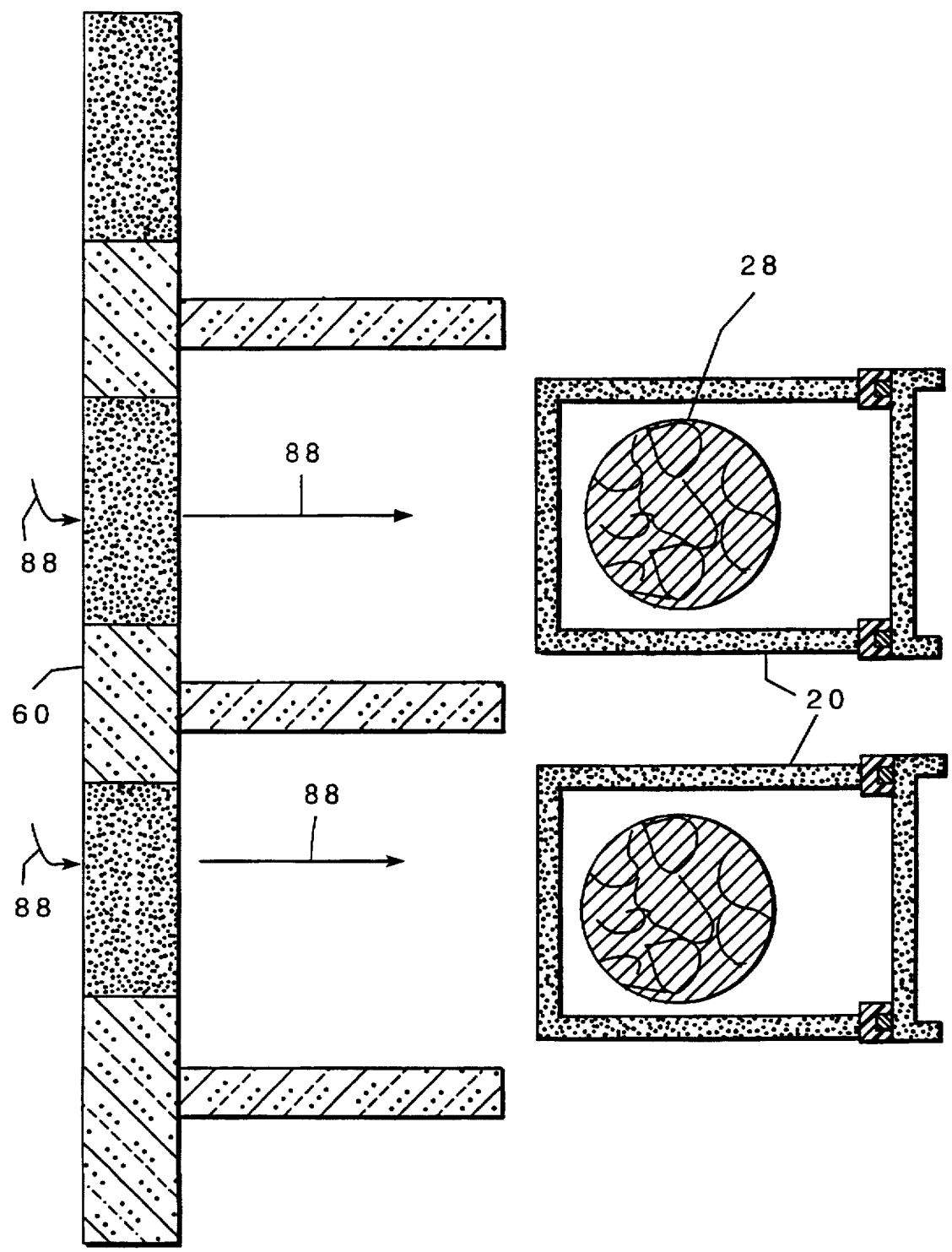

Finally, as shown in FIG. 4G, the end cap wafer 80 is removed, and flow 74 is reversed, as shown by arrows 88, in order to eject the completed capsules 20 from the transfer wafer 60.

The capsules 20 should be maintained in an appropriate aqueous support medium, as known to those skilled in the art of cell culture, for the maintenance of the biological component 28 prior to administration to the host organism.

Administration to the host may be accomplished by injection or by surgical implantation into an appropriate site within the host animal for the purpose of providing the host with the biologically active molecule provided by the encapsulated biologically-active-molecule-producing agent, such as a cell, tissue, or pharmaceutical composition. The host may be an animal, preferably a mammal, and most preferably a human.

It will be apparent to those skilled in the art that any number of possible structures could be fabricated according to the methods disclosed herein. The skilled practitioner will realize that any number of structures may be formed by applying the appropriate photolithographic pattern to a silicon wafer substrate for formation of a mold by the process herein described. For example, by producing a different mold configuration according to the methods described, a structure, such as a sheet, comprising a plurality of capsules may be formed. Moreover, applicants do not intend that the method of the present invention be limited to the fabrication of containment capsules described herein. Instead, a capsule is just one embodiment of a structure produced by the method which is also applicable to the fabrication of other structures, such as microtensile testing machines and disk drive read/write heads.

In summary, microfabricated containment capsules, structural components, methods and apparatus for their filling, and methods for their fabrication and use have been described.

The present invention has been described in terms of preferred embodiments. The invention, however, is not limited to the embodiments depicted and described. Rather, the scope of the invention is defined by the appended claims.

What is claimed is:

1. A microfabricated containment capsule, comprising:
   a shell formed of a thin film inorganic material, said shell having the shape of a right cylinder and including annular walls and planar end faces;
   at least one porous area in said shell, said porous area comprising pores of predetermined, approximately uniform size and distribution;
   said shell providing a selective molecular barrier between the interior and the exterior of said capsule; and
   wherein said annular walls comprise high vertical aspect ratio thin-films and at least one of said end faces comprises a thin-film membrane filter.

2. A containment capsule according to claim 1, wherein said filter is bonded to said annular walls by a sealant.

3. A containment capsule according to claim 2, wherein said sealant is a biocompatible, polymeric material.

4. A containment capsule according to claim 3, wherein said sealant is polyethylene.

5. A method of fabricating a containment capsule, comprising:

forming a mold in a substrate for a shell having at least one opening;
   lining said mold with a sacrificial layer;
   growing a thin film on said sacrificial layer until said mold is filled;
   removing said sacrificial layer to remove said shell from said mold;
   placing an item to be contained within a space defined by said shell; and
   covering the at least one opening in said shell with a microfabricated thin-film membrane filter.

6. A method according to claim 5, wherein said item comprises a biologically-active-molecule-producing agent.

7. A method of fabricating a containment capsule, comprising:
   patterning a masking layer on a substrate with a pattern of discrete perforations, representing a side wall structure of said capsule;
   photoelectrochemically etching holes in the substrate according to said pattern;
   oxidizing and etching said holes until they merge to form a mold;
   lining said mold with a sacrificial layer;
   growing a thin film on said sacrificial layer until said mold is filled;
   forming a first microfabricated thin-film membrane filter on a first open end of said side wall structure;
   etching said sacrificial layer to remove said side wall structure and filter from said mold;
   placing a biologically-active-molecule-producing agent within a space defined by said side wall structure and filter; and
   forming a second microfabricated thin-film membrane filter on a second open end of said side wall structure.

8. A microfabricated containment capsule, comprising:
   a shell formed of a thin film inorganic material, said shell including high vertical aspect thin film side walls and rib members to provide additional structural support for said side walls;
   a first porous area microfabricated at one end of the shell, and a second porous area microfabricated at another end of the shell, the first and second porous areas having opposing faces with an array of pores of predetermined, approximately uniform size and distribution for filtering particles across the opposing faces; and
   said shell providing a selective molecular barrier between the interior and the exterior of said capsule.

9. A microfabricated containment capsule, comprising:
   a shell formed of a thin film inorganic material, said shell having the shape of a right cylinder and including high vertical aspect thin film annular walls and planar end faces;
   a first porous area microfabricated at one end of the shell and a second porous area being microfabricated at another end of the shell, the first and second porous areas having opposing faces with pores of predetermined, approximately uniform size and distribution for filtering particles across the opposing faces; and
   said shell providing a selective molecular barrier between the interior and the exterior of said capsule.

10. A microfabricated containment capsule, comprising:
   a shell formed of a high vertical aspect thin film wall;
   a first porous area microfabricated at one end of the shell and a second porous area being microfabricated at another end of the shell, the first and second porous areas having opposing faces with pores of predetermined, approximately uniform size and distribution for filtering particles across the opposing faces; and
   said shell providing a selective molecular barrier between the interior and the exterior of said capsule;
   wherein said capsule is attached to other like capsules, to form a sheet comprising a plurality of said capsules.

11. A microfabricated containment capsule, comprising:
   a shell formed of a thin film inorganic material, said shell having the shape of a right cylinder and including high vertical aspect thin film annular walls and planar end faces, said shell providing a selective molecular barrier between an interior and an exterior of said capsule; and
   a porous semiconductor substrate portion covering a substantial portion of one of said annular walls or said planar end faces, said porous semiconductor substrate portion having opposing faces with pores of predetermined, approximately uniform size and distribution for filtering particles across the opposing faces.

* * * * *